United States Patent
Schuchman et al.

(10) Patent No.: US 9,155,784 B2
(45) Date of Patent: Oct. 13, 2015

(54) ANTI-TNF-α THERAPY FOR THE MUCOPOLYSACCHARIDOSES AND OTHER LYSOSOMAL DISORDERS

(75) Inventors: Edward H. Schuchman, Haworth, NJ (US); Calogera M. Simonaro, Haworth, NJ (US); Gary E. Striker, New York, NY (US); Helen Vlassara, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 14/128,411

(22) PCT Filed: Jun. 20, 2012

(86) PCT No.: PCT/US2012/043369
§ 371 (c)(1),
(2), (4) Date: Apr. 2, 2014

(87) PCT Pub. No.: WO2012/177778
PCT Pub. Date: Dec. 27, 2012

(65) Prior Publication Data
US 2014/0205584 A1   Jul. 24, 2014

Related U.S. Application Data

(60) Provisional application No. 61/569,452, filed on Dec. 12, 2011, provisional application No. 61/498,946, filed on Jun. 20, 2011.

(51) Int. Cl.
*A61K 31/737* (2006.01)
*A61K 38/46* (2006.01)
*A61K 45/06* (2006.01)

(52) U.S. Cl.
CPC ............ *A61K 38/465* (2013.01); *A61K 31/737* (2013.01); *A61K 38/46* (2013.01); *A61K 45/06* (2013.01)

(58) Field of Classification Search
USPC .......................................................... 514/54
See application file for complete search history.

(56) References Cited

U.S. PATENT DOCUMENTS

2008/0292618 A1 * 11/2008  Weisbart .................... 424/130.1
2010/0160253 A1 *  6/2010  Coombe et al. ................ 514/54
2011/0091442 A1     4/2011  Boyd et al.

FOREIGN PATENT DOCUMENTS

WO    2007095688 A1   8/2007

OTHER PUBLICATIONS

Bielicki et al., "Advantages of Using Same Species Enzyme for Replacement Therapy in a Feline Model of Mucopolysaccharidosis Type VI," The Journal of Biological Chemistry 274(51):36335-36343 (1999).
Simonaro et al., "Involvement of the Toll-like Receptor 4 Pathway and Use of TNF-alpha Antagonists for Treatment of the Mucopolysaccharidoses," PNAS 107(1):222-227 (2010).
Bazian, "Ultra Orphan Drugs for Lysosomal Storage Disorders. A Guideline Comparison and Survey of International Current Practice," 1-70 (2009).
International Search Report and Written Opinion for corresponding PCT Application No. PCT/US2012/043369 (mailed Aug. 31, 2012).
Teichgräber et al., "Ceramide Accumulation Mediates Inflammation, Cell Death and Infection Susceptibility in Cystic Fibrosis," Nature Medicine 14(4):382-391 (2008).
First Office Action and English Translation for Chinese Patent Application No. 201280037341.5 (mailed Dec. 3, 2014).
Partial Supplementary European Search Report for European Patent Application No. 12803458.4 (dated Dec. 1, 2014).
Extended European Search Report for European Patent Application No. 12803458.4 (dated Mar. 20, 2015).
Eliyahu et al., "Anti-TNF-Alpha Therapy Enhances the Effects of Enzyme Replacement Therapy in Rats with Mucopolysaccharidosis Type VI," PLOS ONE 6(8):e22447 (2011).
Schuchman et al., "Pentosan Polysulfate: A Novel Therapy for the Mucopolysaccharidoses," PLOS ONE 8(1):e54459 (2013).
Beutler, E., "Gaucher Disease: New Molecular Approaches to Diagnosis and Treatment," Science 256:794-799 (1992).

* cited by examiner

*Primary Examiner* — Ralph Gitomer
(74) *Attorney, Agent, or Firm* — LeClairRyan, a Professional Corporation

(57) ABSTRACT

The present invention relates to methods of treating a subject with a lysosomal disorder, by administering an agent for enzyme replacement therapy and an agent for anti-TNF-α therapy; by administering a pentosan polysulfate therapy; or by administering a substrate reduction therapy and an anti-TNF-α therapy. The invention further relates to a method of reducing inflammatory cytokines in a subject with a lysosomal disorder that is being treated by enzyme replacement therapy, by administering an agent for anti-TNF-α therapy.

20 Claims, 16 Drawing Sheets

ANTI-TNF-α THERAPY FOR THE MUCOPOLYSACCHARIDOSES AND OTHER LYSOSOMAL DISORDERS

This invention was made with government support under grant number 1R01DK087185 awarded by the National Institutes of Health. The government has certain rights in this invention.

This application is a national stage application under 35 U.S.C. 371 of International Patent Application No. PCT/US2012/043369, filed Jun. 20, 2012, which claims the benefit of U.S. Provisional Patent Application Ser. No. 61/498,946, filed Jun. 20, 2011, and U.S. Provisional Patent Application Ser. No. 61/569,452, filed Dec. 12, 2011, all of which are hereby incorporated by reference in their entirety.

FIELD OF THE INVENTION

The present invention relates to anti-TNF-α therapy for the mucopolysaccharidoses and other lysosomal disorders.

BACKGROUND OF THE INVENTION

Lysosomal storage disorders represent a group of over 40 distinct genetic diseases and are caused by abnormalities of enzymes present in lysosomes. Individuals that are affected with a lysosomal storage disorder present a wide range of clinical symptoms depending upon the specific disorder and the particular genotype involved. The clinical symptoms associated with lysosomal storage disorders can have a devastating impact on affected individuals and their families. For example, reticuloendothelial disease, central nervous system dysfunction, behavioral problems, and severe mental retardation are characteristic of many lysosomal storage disorders. In a specific lysosomal storage disorder group called mucopolysaccharidoses (MPS), other clinical symptoms may include skeletal abnormalities, organomegaly, corneal clouding, and dysmorphic features.

The mucopolysaccharidoses (MPS) are a group of 11 distinct enzyme deficiencies that result in defective catabolism of glycosaminoglycans (GAGs). Neufeld et al., "The Mucopolysaccharidoses," In: METABOLIC AND MOLECULAR BASIS OF INHERITED DISEASE 3421-3452 (Scriver et al., eds McGraw-Hill) (2001). Due to these inherited enzyme defects, glycosaminoglycans (GAGs) progressively accumulate in lysosomes and other intracellular compartments of MPS patients, as well as in extracellular connective tissue matrices. As expected, the major clinical consequences of these enzyme deficiencies are most evident in connective tissue organs, including cartilage, skin, and bone. Major clinical features include a coarse and abnormal facial appearance and cranial development, short limbs, degenerative joint disease, trachea and heart valve defects, and in some cases neurological involvement. Patients are usually born without visible clinical features of MPS, but can develop progressive clinical involvement. In severe cases, an affected child may require constant medical management but still often die before adolescence.

Another type of lysosomal storage disorder, Niemann-Pick disease, also known as sphingomyelin lipidosis, comprises a group of disorders characterized by foam cell infiltration of the reticuloendothelial system. Foam cells in Niemann-Pick become engorged with sphingomyelin and, to a lesser extent, other membrane lipids including cholesterol. Niemann-Pick is caused by inactivation of the enzyme acid sphingomyelinase in Types A and B disease, with more residual enzyme activity in Type B (see Kolodny et al., "Storage Diseases of the Reticuloendothelial System," in NATHAN AND OSKI'S HEMATOLOGY OF INFANCY AND CHILDHOOD 5th ed., vol. 2, 1461-1507 (David G. Nathan and Stuart H. Orkin, Eds., W.B. Saunders Co.) (1998)). The pathophysiology of major organ systems in Niemann-Pick can be briefly summarized as follows. The spleen is the most extensively involved organ of Type A and B patients. The lungs are involved to a variable extent, and lung pathology in Type B patients is the major cause of mortality due to chronic bronchopneumonia. Liver involvement is variable, but severely affected patients may have life-threatening cirrhosis, portal hypertension, and ascites. The involvement of the lymph nodes is variable depending on the severity of disease. Central nervous system involvement differentiates the major types of Niemann-Pick. While most Type B patients do not experience central nervous system involvement, it is characteristic in Type A patients. The kidneys are moderately involved in Niemann Pick disease.

Several approaches have been evaluated for the treatment of these lysosomal storage disorders, including bone marrow transplantation and enzyme replacement therapy. Bone marrow transplantation has proven effective to varying degrees, but, when administered alone, has limited effects on the bones and joints. Clarke, L A, "The Mucopolysaccharidoses: A Success of Molecular Medicine," *Expert Rev. Mol. Med.* 10:e1 (2008). It also is impeded by the deleterious side effects of immunosuppressive and myeloablative medications, and the occurrence of graft versus host disease. The use of cord blood has partially mitigated these complicating factors, although they often remain significant. Enzyme replacement therapy involves the intravenous infusion of recombinant enzymes, usually weekly or biweekly. Clarke, L A, "The Mucopolysaccharidoses: A Success of Molecular Medicine," *Expert Rev. Mol. Med.* 10:e1 (2008). In large part, the effectiveness of enzyme replacement therapy relies on the biodistribution of the infused enzymes, which are readily delivered to the reticuloendothelial organs (e.g., liver, spleen), but less so to other organs. For the MPS disorders, enzyme replacement therapy is available for three types: MPS I (Hurler/Schie Syndrome) (Wraith et al., "Mucopolysaccharidosis Type II (Hunter Syndrome): A Clinical Review and Recommendations For Treatment in the Era of Enzyme Replacement Therapy," *Eur. J. Pediatr.* 167:267-77 (2008); Cox-Brinkman et al., "Ultrastructural Analysis of Dermal Fibroblasts in Mucopolysaccharidosis Type I: Effects of Enzyme Replacement Therapy and Hematopoietic Cell Transplantation," *Ultrastruct. Pathol.* 34:126-32 (2010); Coppa et al., "Effect of 6 Years of Enzyme Replacement Therapy on Plasma and Urine Glycosaminoglycans in Attenuated MPS I Patients," *Glycobiology* 20:1259-73 (2010)); MPS II (Hunter Syndrome) (Glamuzina et al., "Treatment of Mucopolysaccharidosis Type II (Hunter Syndrome) With Idursulfase: The Relevance of Clinical Trial End Points," *J. Inherit. Metab. Dis.* (2011)); and MPS VI (Maroteaux-Lamy Syndrome) (Decker et al., "Enzyme Replacement Therapy for Mucopolysaccharidosis VI: Growth and Pubertal Development in Patients Treated With Recombinant Human N-Acetylgalactosamine 4-Sulfatase," *J. Pediatr. Rehabil. Med.* 3:89-100 (2010); Valayannopoulos et al., "Mucopolysaccharidosis VI Orphanet," *J. Rare Dis.* 12:5 (2010); McGill et al., "Enzyme Replacement Therapy for Mucopolysaccharidosis VI From 8 Weeks of Age—A Sibling Control Study," Clin. Genet. 77:492-498 (2010)). Significant quality-of-life improvements have been noted following enzyme replacement therapy, including improved mobility, breathing, and joint flexibility. However, there is little or no evidence that enzyme replacement therapy directly impacts the cartilage and bone disease in MPS patients, and these positive clinical effects are therefore thought to derive mostly from soft tissue changes (e.g., tendons). Other experimental therapies are also under evaluation for the MPS disorders, including gene therapies (Cotugno et al., "Different Serum Enzyme Levels are Required to Rescue the Various Systemic Features of the Mucopolysaccharidoses," *Hum. Gene Ther.* 21:555-69 (2010); Herati et al., "Radiographic Evaluation of Bones and Joints in Mucopolysaccharidosis I and VII Dogs After Neonatal Gene Therapy," *Mol. Genet. Metab.* 95:142-51 (2008)) and the use of recombinant enzymes fused to cell-specific targeting sequences (Lu et al., "Expression in CHO Cells and Pharmacokinetics and Brain Uptake in the Rhesus Monkey of an IgG-Iduronate-2-Sulfatase Fusion Protein," *Biotechnol. Bioeng.* (2011); Osborn et al., "Minicircle DNA-Based Gene Therapy Coupled With Immune Modulation Permits Long-term Expression of α-L-Iduronidase in Mice With Mucopolysaccharidosis Type I," *Mol. Ther.* 19:450-60 (2011)).

Pentosan polysulfate (PPS) is an FDA-approved, oral medication that has potent anti-inflammatory and clinical effects in animal models of several diseases, including lysosomal storage disorders, and more specifically MPS disorders (this application), as well as arthritis, diabetes, intervertebral disc degeneration, and age-related neurodegeneration. PPS is currently approved for use in patients with interstitial cystitis, and its safety has been demonstrated through clinical testing. PPS inhibits leukocyte recruitment and interferes with some functions of chemokines, cytokines, and growth factors, thereby reducing inflammation and reactive oxygen species (ROS).

Tumor necrosis factor alpha (TNF-α) is believed to play an important role in various disorders, including for example, inflammatory disorders such as rheumatoid arthritis, Crohn's disease, ulcerative colitis, and multiple sclerosis. Both TNF-α and receptors CD120a, CD120b have been studied in great detail. TNF-α in its bioactive form is a trimer and the groove formed by neighboring subunits is important for the cytokine-receptor interaction. Several strategies to antagonize the action of the cytokine have been developed and are currently used to treat various disease states.

A TNF-α inhibitor which has sufficient specificity and selectivity to TNF-α may be an efficient prophylactic or therapeutic pharmaceutical compound for preventing or treating disorders where TNF-α has been implicated as a causative agent. Methods of treating toxic shock (EP Patent No. 0486526 to Rathjen et al.), tumor regression, inhibition of cytotoxicity (U.S. Pat. No. 6,448,380 to Rathjen et al., U.S. Pat. No. 6,451,983 to Rathjen et al., U.S. Pat. No. 6,498,237 to Rathjen et al.), autoimmune disease such as RA and Crohn's disease (EP Patent No. 0663836 to Feldmann et al., U.S. Pat. No. 5,672,347 to Aggarwal et al., U.S. Pat. No. 5,656,272 to Le et al.), graft versus host reaction (U.S. Pat. No. 5,672,347 to Aggarwal et al.), bacterial meningitis (EP Patent No. 0585705 to Hector et al.) by means of an antibody to TNF-α have been described. Previous work has also revealed the important impact of inflammation on the cartilage and bone disease in MPS animal models, and shown that genetic inhibition of Toll-like receptor 4 (TLR4) signaling in knockout mice or the use of TNF-inhibitors in combination with Naglazyme markedly improves cartilage and bone disease. Yet none of the presently available drugs are completely effective for the treatment of lysosomal storage disorders, particularly mucopolysaccharidosis and Niemann-Pick disease. TNF-inhibitors, while effective in the animal models, are intravenous medications that may result in significant side effects, and their long-term use in MPS patients may be difficult to implement.

The present invention is directed to overcoming these and other deficiencies in the art.

SUMMARY OF THE INVENTION

A first aspect of the present invention relates to a method of treating a subject with a lysosomal storage disorder. This method includes selecting a subject with a lysosomal storage disorder and administering to the selected subject an agent for an enzyme replacement therapy, and an agent for an anti-TNF-α treatment under conditions effective to treat the lysosomal storage disorder in the selected subject.

A second aspect of the present invention relates to a method of reducing inflammatory cytokines in a subject with a lysosomal storage disorder that is being treated by an enzyme replacement therapy. This method includes administering to the subject an agent for an anti-TNF-α treatment under conditions effective to reduce the inflammatory cytokines in the subject.

A third aspect of the present invention relates to a method of treating a subject with a lysosomal storage disorder. This method includes selecting a subject with a lysosomal storage disorder and administering pentosan polysulfate (PPS) to the selected subject under conditions effective to treat the lysosomal storage disorder in the selected subject.

A fourth aspect of the present invention relates to a method of treating a subject with a skeletal pathology associated with a lysosomal storage disorder. The method includes selecting a subject with a skeletal pathology associated with a lysosomal storage disorder and administering to the selected subject an agent for substrate reduction therapy and an agent for an anti-TNF-α treatment under conditions effective to treat the lysosomal storage disorder in the subject.

Although enzyme replacement therapy (ERT) is available for several lysosomal storage disorders, the benefit of this treatment to the skeletal system is very limited. Previous work has shown the importance of the Toll-like receptor 4/TNF-α inflammatory pathway in the skeletal pathology of the mucopolysaccharidoses (MPS), and therefore, the present invention examined the additive benefit of combining anti-TNF-α therapy with ERT in a rat model of MPS type VI. In doing so, MPS VI rats were treated for 8 months with Naglazyme® (recombinant human N-acetyl-galactosamine-4-sulfatase), or by a combined protocol using Naglazyme® and the rat-specific anti-TNF-α drug, CNTO1081. Both protocols led to markedly reduced serum levels of TNF-α and receptor activator of nuclear factor kappa-B ligand (RANKL), and the combined treatment reduced TNF-α in the articular cartilage. Analysis of cultured articular chondrocytes showed that the combination therapy also restored collagen IIA1 expression, and reduced expression of the apoptotic marker, PARP. Motor activity and mobility were improved by ERT, and these were significantly enhanced by combination treatment. Tracheal deformities in the MPS VI animals were improved by combination therapy, and there was a modest improvement in bone length. Ceramide levels in the trachea also were markedly reduced. MicroCT analysis did not demonstrate any significant positive effects on bone microarchitecture from either treatment, nor was there histological improvement in the bone growth plates. The results of the present invention demonstrate that combining ERT with anti-TNF-α therapy improved the treatment outcome and led to significant clinical benefit, and that anti-TNF-α therapy improved along improved treatment outcome and led to significant clinical benefit as well. The results also further validate the usefulness of TNF-α, RANKL and other inflammatory molecules as biomarkers for lysosomal storage disorders including MPS disorders.

For the past several years researchers of the present invention have been investigating the joint and bone pathology in MPS animal models, with the long-term goal of developing improved therapies, alone or in conjunction with ERT, BMT, or gene therapy (Simonaro et al., "Bone Marrow Transplantation in Newborn Rats With Mucopolysaccharidosis Type VI: Biochemical, Pathological, and Clinical Findings," *Transplantation* 63:1386-93 (1997); Simonaro et al., "Articular Chondrocytes From Animals With a Dermatan Sulfate Storage Disease Undergo a High Rate of Apoptosis and Release Nitric Oxide and Inflammatory Cytokines: A Possible Mechanism Underlying Degenerative Joint Disease in the Mucopolysaccharidoses," *Lab Investi.* 81:1319-1328 (2001); Simonaro et al., "Joint and Bone Disease in Mucopolysaccharidosis VI and VII: Identification of New Therapeutic Targets and Biomarkers Using Animal Models," *Pediatr. Res.* 57:701-707 (2005), all of which are hereby incorporated by reference in their entirety). As part of this ongoing research, a number of abnormalities in MPS animal models have been identified, including enhanced death (apoptosis) of MPS articular chondrocytes, excessive proliferation of MPS synovial fibroblasts, and disorganization of MPS growth plates. Researchers have also found that the addition of GAGs to the culture media of normal articular chondrocytes induced apoptosis and the release of inflammatory markers, suggesting that GAG storage itself may be an initiating, pro-inflammatory event in the MPS disorders (Simonaro et al., "Mechanism of Glycosaminoglycan-Mediated Bone & Joint Disease: Implications for the Mucopolysaccharidoses & Other Connective Tissue Diseases," *Amer. J. Path.* 172:112-122 (2008), which is hereby incorporated by reference in its entirety). GAG storage in MPS cells also led to activation of the Toll-like receptor 4 (TLR4) signaling pathway, resulting in the release of TNF-$\alpha$ and other inflammatory cytokines.

The present invention, therefore, bred MPS mice (MPS VII, Sly disease) to TLR4 knock-out mice, and found that the double knock-out MPS animals had markedly reduced TNF-$\alpha$, IL1-$\beta$, RANKL and other cytokines, improved bone growth and more organized bone growth plates, and reduced chondrocyte cell death (Simonaro et al., "Involvement of the Toll-Like Receptor 4 Pathway and Use of TNF-Alpha Antagonists for Treatment of the Mucopolysaccharidoses," *Proc. Natl. Acad. Sci.* 107:222-7 (2010), which is hereby incorporated by reference in its entirety). This led researchers to conduct a preliminary analysis of anti-TNF-$\alpha$ therapy in MPS VI rats using CNTO1081, a rat specific equivalent of Remicade®, the FDA-approved anti-TNF-$\alpha$ monoclonal antibody used in arthritis and other inflammatory diseases (Weaver, A L, "Efficacy and Safety of the Anti-TNF Biologic Agents," *Mod. Rheumatol.* 14:101-112 (2004), which is hereby incorporated by reference in its entirety). In that study, it was found that CNTO181 treatment reduced the levels of inflammatory cytokines in MPS VI animals, and also reduced the number of apoptotic articular chondrocytes. However, there was no effect on bone growth or clinical improvements in motor activity. In the current invention, those findings have been extended and evaluated an anti-TNF-$\alpha$ and a combined ERT/anti-TNF-$\alpha$ approach in the MPS VI rats. It was found that the anti-TNF-$\alpha$ approach and combined ERT/anti-TNF-$\alpha$ approach provided several benefits over ERT alone. These included improved gait and motor activity, thinner, less deformed tracheas, and moderately longer bones. Collagen IIA1 expression also was restored in the articular cartilage, and apoptosis was reduced.

The present application is based on the underlying premises that: (a) new therapies are needed for lysosomal storage disorders such as MPS that will improve treatment of the cartilage and bone (including the spine); (b) these therapies must be validated in appropriate animal models prior to their human use; and (c) the severity of disease at the time of treatment will have a major impact on efficacy.

This invention also proposes that PPS may be the first oral medication for MPS, and may also be the first treatment to have a major impact on the cartilage and bone disease in these disorders. This hypothesis is based on: (a) previous studies documenting the important role of inflammation in the pathophyisiology of MPS cartilage and bone disease; (b) the known effects of PPS on inflammation and chondrogenesis; and (c) early preliminary data using PPS in a rat model of one MPS (MPS VI, Maroteaux-Lamy disease). Given that PPS has already been through safety testing and is approved by the FDA, its use in MPS patients also may be "fast-tracked" based on the animal model studies being proposed in the present invention. Of note, since PPS is not expected to enhance residual enzyme activities or lead to GAG reduction in MPS individuals, its use may be combined with ERTs in these disorders. PPS may also be used alone to treat lysosomal storage disorders. PPS is a heparin like GAG molecule. Thus, it would not have been expected to provide benefit to the MPS disorders, which are GAG storage diseases, or other lysosomal storage disorders. In fact, prior to the teachings of the present invention, PPS might have been expected to exacerbate these disorders. The present invention, for the first time, teaches that despite the fact that PPS is a GAG-like molecule, it does provide substantial benefit to MPS and other lysosomal storage disorders.

In summary, treatment of cartilage and bone disease represents an important unmet medical need in the lysosomal storage disorders such as MPS, and the present invention could have a major and rapid impact on the treatment and care of lysosomal storage disorder patients, specifically those with MPS.

BRIEF DESCRIPTION OF THE DRAWINGS

In FIG. 1A, MPS VI rats were subjected to the ERT (black) or combined ERT/anti-TNF-$\alpha$ (gray) treatment for 8 months (n=8/group). Anti-TNF-$\alpha$ therapy was carried out using an antibody against TNF-$\alpha$ (CNTO1081). The animals were euthanized 2 days after the last injection and serum was collected. Age-matched (37 weeks) normal (light gray) and untreated MPS VI (white) sera also were collected, and TNF-$\alpha$ and RANKL levels were determined using immunoassay kits (see Examples, infra). As previously shown, untreated MPS VI animals had markedly elevated levels of these two inflammatory markers, and both were significantly reduced by either ERT or combined treatment (*p<0.005). No significant differences were observed between the two treatment protocols. In FIG. 1B, untreated MPS VI rats exhibited markedly elevated TNF-$\alpha$ immunostaining (red) in the articular cartilage as compared to normal animals, which was modestly reduced by ERT and normalized by combined treatment. In FIG. 1C, hyperplastic synovial membranes (*) with the formation of villi (SV), and invasion of the synovium into the subchondral bone (arrowhead, SB) was evident in untreated MPS VI and ERT-treated synovium. Animals treated with combined therapy exhibited markedly less joint inflammation, although the storage cells were still present.

In FIG. 2A, MPS VI rats were subjected to ERT (boxes) or combined ERT/anti-TNF-$\alpha$ (circles) treatment for 8 months (n=8/group). Anti-TNF-$\alpha$ therapy was carried out using the antibody CNTO1081. Two days after the last injection they were subjected to accelerating rotarod analysis at three different speeds, and their performance was compared to untreated, age and gender-matched MPS VI animals (triangles). At 10 RPM, both groups of treated rats remained on the rotating rod for the maximal time (180 seconds), significantly longer than untreated animals ($p<0.005$). This trend became more pronounced at higher speeds, and there was also a significant distinction between the ERT and combined groups ($p*<0.005$). The times for individual animals are plotted, and the mean value for each group is indicated by the horizontal lines. In FIG. 2B, after treatment the animals also were subjected to gait analysis. Two different colors of food coloring were used to mark the front and hind paws of rats walking through a tube, and the distances between steps and angles of the steps were measured from the paw prints. Each rat was tested at least three times, and a summary of the average paw print values are shown in FIGS. 2A-2B. As can be seen, the angle of rear paw movement was reduced from 60° (untreated) to 45° (compared to untreated $p=0.004$) and 30° (compared to untreated $p=0.0001$) for the ERT and combined treatment animals, respectively. In addition, the distance the animals could move their front paws in each step was increased from 2.8 cm (untreated) to 4.2 cm and significantly to 5.1 cm in the combined treatment group ($p=0.03$). The distance the animals moved their rear paws were not changed in the ERT group, and only modestly increased in the combined group (from 4.9 to 5.1 cm).

In FIG. 3A, MPS VI rats were subjected to the ERT (black) or combined ERT/anti-TNF-α (gray) treatment for 8 months (n=8/group). TNF-α therapy was carried out with the antibody CNT0181. The animals were euthanized 2 days after the last injection, and the femora and tibia were collected for microCT analysis. The results were compared to untreated age and gender-matched MPS VI rats (white), and the values expressed as a percentage of normal controls. ERT did not increase the length of the femora or tibia, while the combined protocol led to increases of ~6 and 14%, respectively. Of note, the tibia and femora in the combined treatment group were on average ~88 and 84% of normal, compared to 74 and 77% in the untreated MPS VI group. FIG. 3B shows a microCT analysis of the coronal views. In untreated and treated MPS VI rats the trabecular density within the metaphyseal bone was reduced, the physeal growth plate was dysmorphic and disrupted, and the epiphyseal trabeculae were disorganized relative to the normal femora. Mild improvement from the combined treatment was detected. FIG. 3C is a microCT analysis of the mid-diaphyseal region of the femora showing axial views with subcortical trabecular infiltration into the marrow space. Although some reductions in trabecular infiltration were noted following treatment, these could not be confirmed by quantitative measures.

In FIG. 4A, tracheas were collected from treated (with antibody CNTO1081) and untreated MPS VI and normal animals at the end of the study (37 weeks of age). As illustrated by this representative figure, untreated MPS VI rats had markedly thickened and abnormal, collapsed tracheas with narrow, flattened interior openings. These abnormalities were not altered by ERT, but were clearly improved by the combined treatment which resulted in rounded tracheas with almost statistically normalized cross sectional areas. FIG. 4B is an immunohistochemical analysis of the tracheas showed increased expression of the pro-inflammatory and pro-apoptotic sphingolipid, ceramide, in the epithelial cells of untreated and ERT-treated animals (red), consistent with the occurrence of inflammatory disease. Tracheas from the combined treatment group showed almost normal ceramide expression.

In FIG. 5A, MPS VI rats were subjected to the ERT or combined ERT/anti-TNF-α treatment for 8 months (n=8/group). Anti-TNF-α therapy was carried out using the antibody CNTO1081. The animals were euthanized 2 days after the last injection, and articular chondrocytes were isolated and processed for western blotting (FIG. 5A). As shown in this representative experiment, ERT alone increased expression of collagen X, and to a more modest degree collagen IIA1. Similar observations were seen in the combined treatment group, except that the levels of collagen IIA1 expression were even more pronounced. To confirm these observations, immunofluorescent microscopic analysis of collagen IIA1 was carried out on articular cartilage sections from untreated, ERT-treated, and combined treatment animals (FIG. 5B). As evident in FIG. 5B, higher collagen IIA1 expression (red) was present in the combined treatment group, similar to normal. The expression of the apoptosis marker, PARP, also was examined in the treated and control animals by western blotting, and was only reduced by combined treatment. In addition, the levels of the aggrecanase, ADAMTS5, which is elevated in MPS VI, was reduced by both treatment protocols.

FIG. 10A is an immunohistochemical analysis of liver and spleen in PPS treated MPS VI rats showed decreased TNF-α expression when compared to untreated age-matched 9-month-old MPS animals. In FIG. 10B, serum TNF levels were also decreased in the PPS treated animals.

In FIGS. 12A and 12B, one-month old MPS VI rats were maintained for eight months on normal water or with water containing 25 mg/day PPS (n=6/group). Representative images are shown. Arrows indicate ocular porphyrin secretions, wide broad skull and snout and small ears in the untreated, with marked improvement in the treated animal. In FIG. 12C, animals were tested on an accelerating rotarod apparatus. The treated MPS VI rats could remain on the rotating rod more than twice as long as untreated rats at 20 RPM. In addition, only normal and treated rats were able to remain on the rotating rod at speeds up to 35 RPM (60% of normal).

FIG. 14A shows Safranin-O/fast green staining of normal control (left) and MPS VI (right) animals. FIG. 14B illustrates biomechanical results of lumbar motion segments indicated MPS animals had a lower neutral zone stiffness and compressive creep time constant, and suggested diminished collagen integrity and GAG function. FIG. 14C shows sagittal radiographs of control, MPS and treated (T) groups indicated that the disc height index (DHI, defined as the intervertebral disc height normalized by the average height of the 2 adjacent vertebrae) was greater for MPS than control, and PPS treatment of skeletally mature animals (6 months of age) did not influence this parameter, motivating earlier intervention.

DETAILED DESCRIPTION OF THE INVENTION

Figures 1A, 1B, 1C:
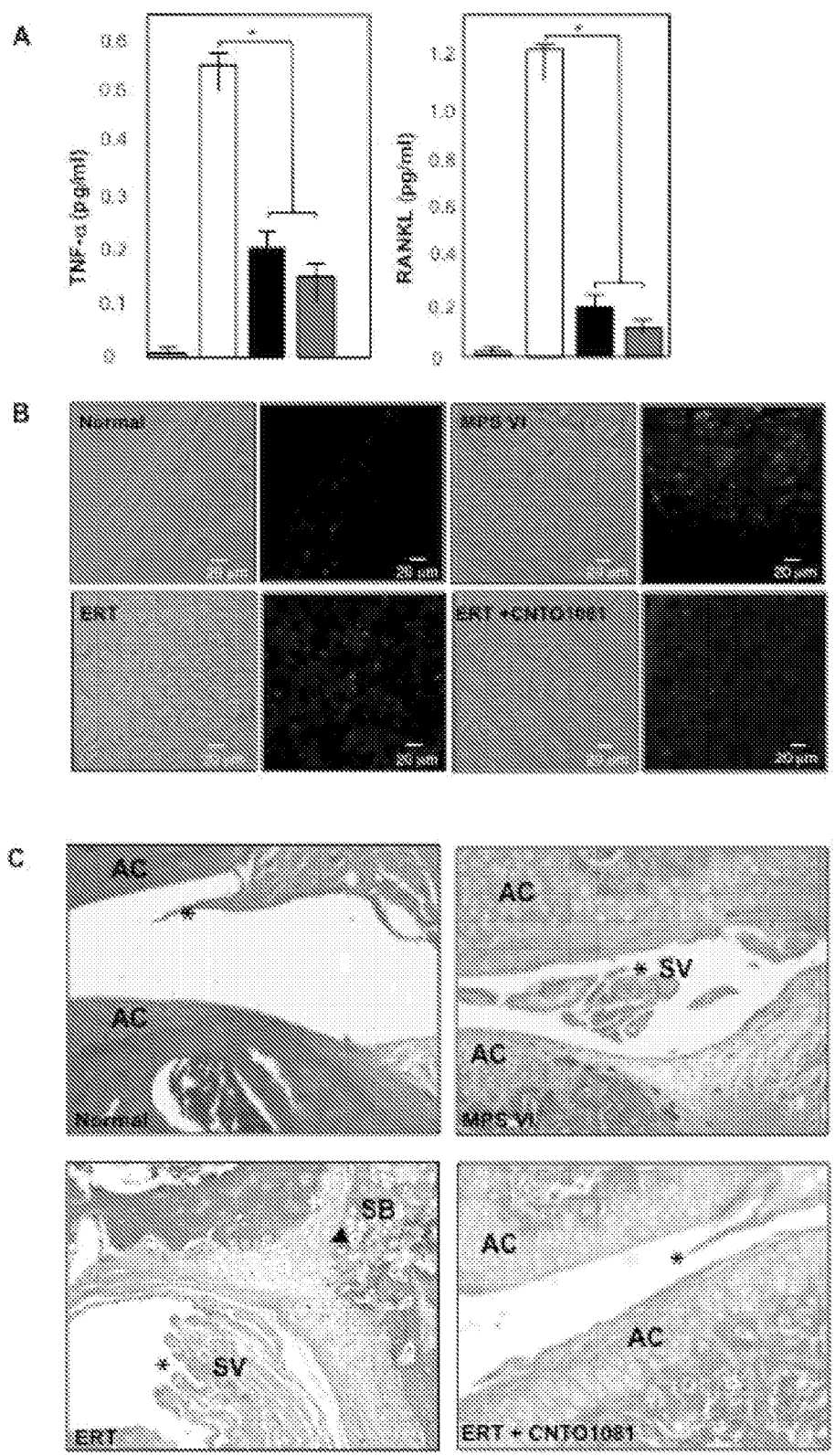
FIGS. 1A-1C illustrate anti-inflammatory effects of ERT and combined ERT/anti-TNF-$\alpha$ therapy in MPS VI rats.

A first aspect of the present invention relates to a method of treating a subject with a lysosomal storage disorder. This method includes selecting a subject with a lysosomal storage disorder and administering to the selected subject an agent for an enzyme replacement therapy, and an agent for an anti-TNF-α treatment under conditions effective to treat the lysosomal storage disorder in the selected subject.

A lysosomal storage disorder according to the present invention is any disorder where the existence or accumulation of a lysosomal enzyme substrate occurs due to a deficiency in a lysosomal enzyme, such that an undesired effect is produced (e.g., abnormal accumulation of substrate or production of an abnormal substrate). The lysosomal enzyme may be produced in abnormal amounts (e.g., the enzyme may not be expressed at all in a subject, may be expressed at low levels or may be expressed at high levels) or may function abnormally, for example, due to a mutation or improper protein folding. A lysosomal enzyme according to the present invention is any hydrolytic enzyme contained in the lysosomal compartment of a cell that metabolizes cellular byproducts contained therein. A substrate as used herein refers to a lysosomal substrate for one or more lysosomal enzymes. No particular limitation is imposed on the lysosomal storage disorders, which are to be treated by the methods of the present method, so long as the lysosomal storage disorders are disorders recognized as such in the art.

Lysosomal storage disorders of the invention can be subdivided into the following disease states: sphingolipidoses, mucopolysaccharidoses, glycoproteinoses, mucolipidoses, glycogenosis type II, ceroid lipofuscinoses, and those that fall under the category of "other" (Caillaud et al., "Gene Therapy in Lysosomal Diseases," *Biomed. Pharmacother.* 54: 505-12 (2000); Nathan and Oski, HEMATOLOGY OF INFANCY AND CHILDHOOD, Chapter 35, W.B. Saunders (2003), both of which are hereby incorporated by reference in their entirety). Nearly all lysosomal storage disorders are autosomal recessive. Two noted exceptions to this are Fabry's Disease and Hunter's Syndrome, which are X-linked. (U.S. Patent Application 20070009500 to Blazar et al., which is hereby incorporated by reference in its entirety).

The lysosomal storage disorder of the present invention can include, but is not limited to, sphingolipidoses, mucopolysaccharide storage disease (mucopolysaccharidoses), glycoproteinoses, mucolipidoses, glycogenosis type II, ceroid lipofuscinoses, and other abnormalities of lysosomal protein function. More specifically, the disorder can be, but is not limited to, GM1 gangliosidosis (Landing's disease), GM2 gangliosidosis variant B/B1 (Tay-Sach's disease) and variant 0 (Sandhoffs disease), metachromatic leukodystrophy, Krabbe's disease, Fabry's disease, Gaucher's disease, Niemann-Pick disease (A, B, C), Farber's disease, Wolman's disease, Austin's disease, mucopolysaccharidoses type I (Hurler's disease or Hurler's Syndrome), Scheie's disease, Hurler-Scheie's disease, type II (Hunter's disease), type III (Sanfilippo's disease, type III A through D, type IV (Morquio's disease), type IV A and B, type VI (Maroteaux-Lamy's disease), type VII (Sly's disease), type IX, pycnodysostosis, aspartylglucosaminuria, fucosidosis, α-mannosidosis, β-mannosidosis, Schindler's disease, Kanzaki's disease, mucolipidoses type I (sialidosis), type IB (galactosialidosis), and type II, III, and IV (mucolipidoses), Glycogenosis type II (characterized by Pompe's disease), Santavuori-Haltia disease, Jansky-Bielshowsky disease, Batten disease, Kufs disease, disease states characterized by mutations in the CLN5, CLN6, CLN7, and CLN8 loci, and/or other lysosomal storage diseases, such as sialic acid storage diseases (infantile form, Salla disease), and methylmalonic aciduria (U.S. Patent Publication No. 2007/0009500 to Blazar et al.; U.S. Pat. No. 7,951,545 to Okamura et al., both of which are hereby incorporated by reference in their entirety).

In one embodiment of the present invention, the lysosomal storage disorder is a sphingolipidosis, where the sphingolipidosis is Niemann-Pick disease, a disease in which sphingomyelin is accumulated. Niemann-Pick type B is due to an impediment in acid sphingomyelinase, and Niemann-Pick type C is due to a cholesterol esterification defect. Other examples of sphingolipidoses include the following diseases, but are not limited to these diseases: $GM_1$ gangliosidosis (Landing's disease; β-galactosidase deficiency), $GM_2$ gangliosidosis variant B/B1 (Tay-Sach's disease; hexosaminidase A deficiency) and variant 0 (Sandhoffs disease, hexosaminidase A and B deficiency), metachromatic leukodystrophy (arylsulfatase A deficiency), Krabbe's disease (galactosylceramidase deficiency), Fabry's disease (α-galactosidase deficiency), Gaucher's disease (deficiency in β-glucosidase), Niemann-Pick disease (A, B, C; sphingomyelinase deficiency), Farber's disease (deficiency in ceramidase), Wolman's disease (deficiency in acid lipase), and Austin's disease (deficiency in multiple sulfatases). (U.S. Patent Publication No. 2007/0009500 to Blazar et al., which is hereby incorporated by reference in its entirety).

In another embodiment of the present invention, the lysosomal storage disorder is mucopolysaccharidosis. The term mucopolysaccharidosis (MPS), as used herein refers to a subgroup of lysosomal storage disorders characterized by the accumulation and storage of GAG within lysosomes. In one particular embodiment, the mucopolysaccharidosis according to the present invention may include MPS I (Hurler/Schie Syndrome), MPS II (Hunter Syndrome), MPS VI (Maroteaux-Lamy Syndrome), MPS III (Sanfilippo Syndrome), MPS IV (Morquio Syndrome), and/or MPS VII (Sly Disease). Additional examples of classes of mucopolysaccharidoses Types I through 1× and the deficient enzymes are listed in Table 1 that may be treated by the methods of the present invention include those listed in Table 1, infra (U.S. Pat. No. 7,951,545 to Okamura et al., which is hereby incorporated by reference in its entirety).

TABLE 1

Classes of Mucopolysaccharidoses

| Class name | | Lacking enzyme |
|---|---|---|
| IH | Hurler syndrome | α-L-iduronidase |
| IS | Scheie syndrome | α-L-iduronidase |
| IH/S | Hurler-Scheie syndrome | α-L-iduronidase |

TABLE 1-continued

Classes of Mucopolysaccharidoses

| Class name | | Lacking enzyme |
|---|---|---|
| IIA | Hunter syndrome, severe type | sulfoiduronate sulfatase |
| IIB | Hunter syndrome, mild type | sulfoiduronate sulfatase |
| IIIA | Sanfitippo syndrome A | heparan sulfate N-sulfatase |
| IIIB | Sanfitippo syndrome B | N-acetyl-α-D-glucosaminidase |
| IIIC | Sanfitippo syndrome C | acetyl-CoA-α-glucosaminide N-acetyltransferase |
| IIID | Sanfitippo syndrome D | N-acetylglucosamine-6-sulfatase |
| IVA | Morquto syndrome A | N-acetylgalactosamine-6-sulfatase |
| IVB | Morquto syndrome B severe type | β-galactosidase |
| VIB | Maroteaux-Lamy syndrome/mild type | N-acetylgalactosamine-4-sulfatase |
| VII | β-glucuronidase deficiency | β-glucuronidase |

Glycoproteinoses according to the present invention comprise the following diseases, but are not limited to these diseases: aspartylglucosaminuria (deficiency in N-acetyl β-glucosaminidase), fucosidosis (deficiency in α-fucosidase), α-mannosidosis (α-mannosidase deficiency), α-mannosidosis (β-mannosidase deficiency), Schindler's disease, and Kanzaki's disease (α-N-acetylgalactosaminidase or α-galactosidase B, for both Schindler's and Kanzaki's disease) (U.S. Patent Publication No. 2007/0009500 to Blazar et al., which is hereby incorporated by reference in its entirety).

Mucolipidoses of the present invention include, but are not limited to, diseases: type I (sialidosis; α-neuraminidase deficiency), type IB (galactosialidosis; Cathepsin A deficiency), and type II, III, and IV (mucolipidoses; N-acetylglucosamine-1-phosphotransferase). Glycogenosis type II is characterized, for example, by Pompe's disease (deficiency in α-1,4-glucosidase or acid maltase) (U.S. Patent Publication No. 2007/0009500 to Blazar et al., which is hereby incorporated by reference in its entirety).

Ceroid lipofuscinoses of the present invention include, but are not limited to, Santavuori-Haltia disease (palmitoyl protein thioesterase deficiency), Jansky-Bielshowsky disease (tripeptidyl peptidase I deficiency), Batten disease (CLN3 protein deficiency), Kufs disease, and disease states characterized by mutations in the CLN5, CLN6, CLN7, and CLN8 loci (U.S. Patent Publication No. 2007/0009500 to Blazar et al., which is hereby incorporated by reference in its entirety).

Other lysosomal storage diseases include, but are not limited to, sialic acid storage diseases (infantile form, Salla disease; deficient in sialic acid carrier), and methylmalonic aciduria (deficient in vitamin B12 carrier protein) (U.S. Patent Publication No. 2007/0009500 to Blazar et al., which is hereby incorporated by reference in its entirety).

The term enzyme replacement therapy, as used herein refers to any drug or therapy that replaces a deficient or defective enzyme in a subject with a lysosomal storage disorder.

Enzyme Replacement Therapy ("ERT") according to the present invention involves administration, preferably intravenous, of an exogenously-produced natural or recombinant enzyme. Following administration, the replacement enzymes are secreted by the liver into systemic circulation. Both adjacent and distant cells recapture the secreted enzymes, primarily through the mannose-6-phosphate receptor, which is present on the surface of virtually all cells (Suzuki, K. "Lysosomal Diseases," in: GREENFIELD'S NEUROPATHOLOGY 653-735 (Graham, D. I., Lantos, P. K. eds., Arnold: London) (2002), which is hereby incorporated by reference in its entirety). Localized administration of enzyme can replenish at least part of the enzyme population in deficient cells. However, these enzymes generally have short circulating and intracellular half-lives, and therapy requires regular parenteral administration of relatively large amounts of the relevant enzyme (U.S. Patent Publication No. 2007/0009500 to Blazar et al., which is hereby incorporated by reference in its entirety). Enzyme replacement therapy proof-of-principle has been established in a Hurler animal model (Shull et al., "Enzyme Replacement in a Canine Model of Hurler Syndrome," *Proc. Natl. Acad. Sci. USA* 91:12937-12941 (1994), which is hereby incorporated by reference in its entirety). Others have developed effective methods for cell culture expression of recombinant enzyme in sufficient quantities to be collected for therapeutic use (Kakkis et al., "Overexpression of the Human Lysosomal Enzyme α-L-Iduronidase in Chinese Hamster Ovary Cells," *Prot. Express. Purif.* 5:225-232 (1994), which is hereby incorporated by reference in its entirety). In one embodiment of the present invention, enzyme replacement therapy may be include, but is not limited to, Alglucerase, Imiglucerase, Velaglucerase Alfa, Laronidase, Agalsidase Beta, Galsulfase, Algluscosidase Alfa, N-acetylgalactosamine-6 sulfatase, and Idursulfase.

Enzyme replacement therapy is particularly effective when treating certain lysosomal storage diseases. For example, enzyme replacement in the treatment of Gaucher's and Fabry's disease has been effective in reversing non-neuropathic symptoms of these diseases (Weinreb et al., "Effectiveness of Enzyme Replacement Therapy in 1028 Patients With Type 1 Gaucher Disease After 2 to 5 Years of Treatment: A Report From the Gaucher Registry," *Am. J. Med.* 113:112-119 (2002); Schiffman et al., "Enzyme Replacement Therapy in Fabry Disease: A Randomized Controlled Trial," *JAMA* 285: 2743-2749 (2001), both of which are hereby incorporated by reference in their entirety). However, in many lysosomal storage diseases, such as mucopolysaccharidosis type I (i.e., MPS-1H; Hurler's Syndrome), replacement of enzyme can result in potent immunogenic responses against the infused donor proteins. Further, systemically administered enzymes are unable to access sites that arise later in development, such as the CNS and skeletal system. Thus, enzyme replacement therapy is not effective in correcting neurological manifestations and skeletal defects associated with many of these metabolic storage diseases (U.S. Patent Publication No. 2007/0009500 to Blazar et al., which is hereby incorporated by reference in its entirety).

The term anti-TNF-α therapy, as used herein refers to any drug or therapy that replaces deficient or defective TNF-α in a subject with a lysosomal storage disorder. In one embodiment of the present invention, the agent for anti-TNF-α therapy is selected from the group consisting of Infliximab, Adalimumab, Etanercept, Golimumab, and Natalizumab. In another embodiment, the agent for anti-TNF-α therapy is pentosan polysulfate (PPS).

For purposes of this and other aspects of the invention, the target subject encompasses any animal, preferably a mammal, more preferably a human. In the context of administering a composition of the invention for purposes of preventing a treating patient with a lysosomal storage disorder, the target subject encompasses any subject that is at risk of being infected by a lysosomal storage disorder. Particularly susceptible subjects include infants and juveniles, as well as immunocompromised adults. In the context of administering a composition of the invention for purposes of treating a lysosomal storage disorder in a subject, the target subject population encompasses any subject infected with any type of lysosomal storage disorder. Particularly suitable subjects include those at risk of infection or those infected with MPS I, MPS II, MPS III, MPS IV, MPS VI, or MPS VII. Mucopolysaccharidoses, in particular, are generally asymptomatic in newborns (i.e., infants), but onset thereof becomes clear by manifestations including arrested height gain, abnormal development of bones, and abnormal development of facial appearance, skin, and hair, during infancy or childhood. In some cases, although subjects are normal during neonatal periods, mental retardation gradually progresses over years. Therefore, diagnosis and treatment of mucopolysaccharidoses, etc. in an early newborn stage and infancy during which no clinical syndromes are manifested may possibly prevent mental retardation, etc., through early enzyme replacement therapy, genetic treatment, or bone marrow transplantation. Accordingly, diagnosis and treatment of mucopolysaccharidoses may be performed for newborns and infants (U.S. Pat. No. 7,951,545 to Okamura et al., which is hereby incorporated by reference in its entirety). In one embodiment of the present invention, the subject may be an infant or juvenile. In another embodiment, the subject may be an adult.

As used herein, an effective amount means an amount which provides the desired local or systemic effect. For example, an effective dose is an amount sufficient to effect a beneficial or desired clinical or non-clinical result. Therapeutically effective amounts of agents for enzyme replacement therapy, and agents for anti-TNF-α therapy can be determined in accordance with standard procedures, which take numerous factors into account, including, for example, the concentrations of these active agents in the composition, the mode and frequency of administration, the severity of the lysosomal storage disorder to be treated (or prevented), and subject details, such as age, weight, and overall health and immune condition. General guidance can be found, for example, in the publications of the International Conference on Harmonization and in REMINGTON'S PHARMACEUTICAL SCIENCES (Mack Publishing Company 1990), which is hereby incorporated by reference in its entirety. A clinician may administer enzyme replacement therapeutics or anti-TNF-α therapeutics, until a dosage is reached that provides the desired or required prophylactic or therapeutic effect. The progress of this therapy can be easily monitored by conventional assays.

Therapeutically effective amount of the enzyme replacement therapeutic agents and anti-TNF-α therapeutic agents typically are at least 1 mg composition per kilogram of body weight (mg/kg), including at least 2 mg/kg, at least 5 mg/kg, at least 25 mg/kg, at least 50 mg/kg, at least 100 mg/kg, at least 150 mg/kg, at least 200, at least 250 mg/kg, at least 500 mg/kg, at least 750 mg/kg, and at least 1000 mg/kg, per dose or on a daily basis. Enzyme replacement therapy and anti-TNF-α therapy is usually administered on multiple occasions. Intervals between single dosages can be weekly, monthly, or yearly. Intervals can also be irregular as indicated by measuring blood levels of antibody in the subject. Alternatively, enzyme replacement therapy and anti-TNF-α therapy can be administered as a sustained release formulation, in which case less frequent administration is required. The dosage and frequency of administration can vary depending on whether the treatment is prophylactic or therapeutic. In prophylactic applications, a relatively low dosage is administered at relatively infrequent intervals over a long period of time. In therapeutic applications, a relatively high dosage at relatively short intervals is sometimes required until progression of the disease is reduced or terminated and, preferably, until the subject shows partial or complete amelioration of symptoms of disease. In one embodiment of the present invention, the administering is repeated.

The enzyme replacement therapeutic agents and anti-TNF-α therapeutic agents of the present invention can be administered as part of a combination therapy in conjunction with another active agent, depending upon the nature of the lysosomal storage disorder that is being treated. In one embodiment of the present invention, the method includes administering an additional therapy. Exemplary forms of additional therapy according to the present invention include, but are not limited to, bone marrow transplant, chaperone therapy, and gene therapy. Bone marrow transplantation, in particular, is a therapeutic approach to the treatment of lysosomal storage disorders. Bone marrow transplantation reconstitutes a patient's hematopoietic system with stem cells from healthy immunocompatible donors to establish life-long sources of enzyme (Steward, C. G., "Bone Marrow Transplantation for Genetic Diseases," in: BLOOD CELL BIOCHEMISTRY. VOLUME 8: HEMATOPOIESIS AND GENE THERAPY 13-56 (Fairbairn, L. J., Testa, N. G. eds., New York: Klewer Academic/Plenum Publishers.) (1999), which is hereby incorporated by reference in its entirety). Hundreds of patients with lysosomal storage disorders have been treated by transplantation for many years. For example, it has been reported that treatment of non-neuropathic Gaucher's disease by bone marrow transplantation resulted in almost a complete reversal of symptoms (Hoogerbrugge et al., "Allogeneic Bone Marrow Transplantation for Lysosomal Storage Diseases. The European Group for Bone Marrow Transplantation," *Lancet* 345:1398-1402 (1995); see U.S. Patent Publication No. 2007/0009500 to Blazar et al., both of which are incorporated by reference in their entirety).

Gene therapy according to the present invention refers to a method of changing the expression of an endogenous gene by exogenous administration of a gene. As used herein, gene therapy also refers to the replacement of defective gene encoding a defective protein, or replacement of a missing gene, by introducing a functional gene corresponding to the defective or missing gene into somatic or stem cells of an individual in need. Gene therapy can be accomplished by ex vivo methods, in which differentiated or somatic stem cells are removed from the individual's body followed by the introduction of a normal copy of the defective gene into the explanted cells using a viral vector as the gene delivery vehicle. In addition, in vivo direct gene transfer technologies transfer genes into cells in the individual in situ using a broad range of viral vectors, liposomes, protein DNA complexes or naked DNA in order to achieve a therapeutic outcome. See U.S. Pat. No. 7,446,098 to Fan, which is hereby incorporated by reference in its entirety.

Types and methods of gene therapy that may be used in the present invention are well known in the art (Fairbairn et al., "Long-Term In Vitro Correction of α-L-Iduronidase Deficiency (Hurler Syndrome) in Human Bone Marrow," *Proc. Natl. Acad. Sci. U.S.A.* 93:2025-2030 (1996); Kolodny et al., "Storage Diseases of the Reticuloendothelial System," In: NATHAN AND OSKI'S HEMATOLOGY OF INFANCY AND CHILDHOOD, 5th ed., vol. 2, pages 1461-1507 (Nathan and Orkin, Eds., W.B. Saunders Co.) (1998); Medin et al., "Correction in Trans for Fabry Disease: Expression, Secretion, and Uptake of α-Galactosidase A in Patient-Derived Cells Driven by a High-Titer Recombinant Retroviral Vector," *Proc. Natl. Acad. Sci. USA* 93:7917-7922 (1996); Pauly et al., "Complete Correction of Acid α-Glucosidase Deficiency in Pompe Disease Fibroblasts in Vitro, and Lysosomally Targeted Expression in Neonatal Rat Cardiac and Skeletal Muscle," *Gene Therapy* 5:473-480 (1998); Zaretsky et al., "Retroviral Transfer of Acid α-Glucosidase cDNA to Enzyme-Deficient Myoblasts Results in Phenotypic Spread of the Genotypic Correction by Both Secretion and Fusion," *Human Gene Therapy* 8:1555-1563 (1997), all of which are hereby incorporated herein by reference in their entirety; see also WO 1998/041240, which is hereby incorporated herein by reference in their entirety). A frequently used method for administration of gene therapy according to the present invention, both in vivo and ex vivo, is the use of viral vectors for delivery of the gene. Many species of virus are known, and many have been extensively studied for gene therapy purposes. The most commonly used viral vectors include those derived from adenovirus, adeno-associated virus (AAV) and retrovirus, including lentivirus such as human immunodeficiency virus (HIV). See WO 99/57296, WO 99/41399, and U.S. Patent Publication No. 2011/0142818 to Meeker et al., all of which are hereby incorporated by reference in their entirety. Gene therapy according to the present invention is contemplated both with replacement genes such as glucocerebrosidase or with inhibitory RNA (siRNA) for the SNCA gene. See U.S. Pat. No. 7,446,098 to Fan, which is hereby incorporated by reference in its entirety.

The enzyme replacement therapy and anti-TNF-α therapy of the present invention may be administered in a single dose, or in accordance with a multi-dosing protocol. For example, relatively few doses of the therapeutic composition are administered, such as one or two doses. In embodiments that include conventional therapy, which generally involves multiple doses over a period of days or weeks, the enzyme replacement therapy or anti-TNF-α therapy can be taken one, two or three or more times daily for a period of time, such as for at least 5 days, 10 days or even 14 or more days. However, the different dosages, timing of dosages and relative amounts of the therapeutic composition and antibiotics can be selected and adjusted by one of ordinary skill in the art. In one embodiment, the administering is repeated.

Agents of the present invention can be administered orally, by inhalation, by intranasal instillation, topically, transdermally, parenterally, subcutaneously, by intravenous injection, by intra-arterial injection, by intramuscular injection, intraplurally, intraperitoneally, or by application to mucous membrane. The most typical route of administration is intravenous injection.

The pharmaceutical agents of the present invention may be formulated for parenteral administration. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the pharmaceutical agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Any method known to the skilled artisan may be used to monitor mucopolysaccharidoses status and the effectiveness of a therapy of the invention. Clinical monitors of disease status may include but are not limited to organ volume (e.g. liver, spleen), hemoglobin, erythrocyte count, hematocrit, thrombocytopenia, cachexia (wasting), and plasma chitinase levels (e.g. chitotriosidase). Chitotriosidase, an enzyme of the chitinase family, is known to be produced by macrophages in high levels in subjects with lysosomal storage diseases (see Guo et al., "Elevated Plasma Chitotriosidase Activity in Various Lysosomal Storage Disorders," *J. Inherit. Metab. Dis.* 18, 717-722 (1995); den Tandt et al., "Marked Increase of Methylumbelliferyl-tetra-N-acetylchitotetraoside Hydrolase Activity in Plasma From Gaucher Disease Patients," *J. Inherit. Metab. Dis.* 19, 344-350 (1996); Dodelson de Kremer et al., "Plasma Cchitotriosidase Activity in Argentinian Patients With Gaucher Disease, Various Lysosomal Diseases and Other Inherited Metabolic Disorders," *Medicina* (Buenos Aires) 57, 677-684 (1997); Czartoryska et al., "Changes in Serum Chitotriosidase Activity With Cessation of Replacement Enzyme (Cerebrosidase) Administration in Gaucher Disease," *Clin. Biochem.* 33, 147-149 (2000); Czartoryska et al., "Serum Chitotriosidase Activity in Gaucher Patients on Enzyme Replacement Therapy (ERT)," *Clin. Biochem.* 31, 417-420 (1998); Mistry et al., "A Practical Approach to Diagnosis and Management of Gaucher's Disease," *Baillieres Clin. Haematol.* 10, 817-838 (1997); Young et al., "Plasma Chitotriosidase Activity in Gaucher Disease Patients who Have Been Treated Either by Bone Marrow Transplantation or by Enzyme Replacement Therapy With Alglucerase," *J. Inherit. Metab. Dis.* 20, 595-602 (1997); Hollak et al., "Marked Elevation of Plasma Chitotriosidase Activity. A Novel Hallmark of Gaucher Disease," *J. Clin. Invest.* 93, 1288-1292 (1994), all of which are hereby incorporated by reference in their entireties).

In one embodiment of the present invention, the subject has a skeletal pathology associated with a lysosomal storage disorder. Skeletal pathologies that are associated with lysosomal storage disorders include, but are not limited to, bone length, bone shaft width expansion, width of bone growth plates, tissue mineral density, trachea circumference, locomotor function, articular chondrocytes, gait analysis, and by inflammatory markers such as ceramide levels, TNF-α levels, RANKL levels, and collagen expression. Mild skeletal pathologies may include joint stiffness and hepatosplenomegaly. These examples of skeletal pathology may be used as markers to monitor the status of progression or regression of lysosomal storage disorders described supra.

Methods for measuring markers and monitoring status of lysosomal storage disorders are well known in the art and include, but are not limited to, immunohistochemistry, immunoblot analysis, serum immunoassays, and western blot analysis.

A second aspect of the present invention relates to a method of reducing inflammatory cytokines in a subject with a lysosomal storage disorder that is being treated by an enzyme replacement therapy. This method includes administering to the subject an agent for an anti-TNF-α treatment under conditions effective to reduce the inflammatory cytokines in the subject.

Inflammatory cytokines that may be reduced by the methods of the present invention include, but are not limited to, TNF-α, RANKL, and IL1-β. TNF-α, in particular, may be reduced by the methods of the present invention. TNF-α is a pleiotropic cytokine that is primarily produced by activated macrophages and lymphocytes; but is also expressed in endothelial cells and other cell types. TNF-α is a major mediator of inflammatory, immunological, and pathophysiological reactions. (Grell et al., "The Transmembrane Form of Tumor Necrosis Factor is the Prime Activating Ligand of the 80 kDa Tumor Necrosis Factor Receptor," *Cell* 83:793-802 (1995), which is hereby incorporated by reference in its entirety). Two distinct forms of TNF exist, a 26 kDa membrane expressed form and the soluble 17 kDa cytokine which is derived from proteolytic cleavage of the 26 kDa form. The soluble TNF polypeptide is 157 amino acids long and is the primary biologically active molecule. TNF-α exerts its biological effects through interaction with high-affinity cell surface receptors. Two distinct membrane TNF-α receptors have been cloned and characterized. These are a 55 kDa species, designated p55 TNF-R and a 75 kDa species designated p75 TNF-R (Corcoran et al., "Characterization of Ligand Binding by the Human p55 Tumour-Necrosis-Factor Receptor. Involvement of Individual Cysteine-Rich Repeats," *Eur. J. Biochem.* 223:831-840 (1994), which is hereby incorporated by reference in its entirety). The two TNF receptors exhibit 28% similarity at the amino acid level. This is confined to the extracellular domain and consists of four repeating cysteine-rich motifs, each of approximately 40 amino acids. Each motif contains four to six cysteines in conserved positions. Dayhoff analysis shows the greatest intersubunit similarity among the first three repeats in each receptor. This characteristic structure is shared with a number of other receptors and cell surface molecules, which comprise the TNF-R/nerve growth factor receptor superfamily (Corcoran et al., "Characterization of Ligand Binding by the Human p55 Tumour-Necrosis-Factor Receptor. Involvement of Individual Cysteine-Rich Repeats," *Eur. J. Biochem.* 223:831-840 (1994), which is hereby incorporated by reference in its entirety).

In one embodiment, the method includes selecting a subject with a skeletal pathology associated with a lysosomal disorder as described supra, to be subjected to the administering.

This second aspect is carried out in accordance with the previous described aspect. Modes of administration and therapeutically effective dosing related to this aspect of the invention are described supra.

A third aspect of the present invention relates to a method of treating a subject with a lysosomal storage disorder. This method includes selecting a subject with a lysosomal storage disorder and administering pentosan polysulfate (PPS) to the selected subject under conditions effective to treat the lysosomal storage disorder in the selected subject.

Pentosan polysulfate according to the present invention includes a sulfated, semi-synthetic polysaccharide composed of β-D-xylopyranose residues having a molecular weight in the range of 1,500 to 6,000 Daltons and its pharmaceutically-acceptable salts. The compound is described in The Merck Index, Eleventh Edition, Merck & Co, Inc., Rahway, N.J. (1989), pg. 7093; U.S. Pat. No. 5,180,715 to Parsons; U.S. Pat. No. 5,643,892 to Striker et al.; and U.S. Patent Publication No. 2001/0034328 to Cartt et al., all of which are hereby incorporated by reference in their entirety.

It should be appreciated that pentosan polysulfate is often formulated as a salt, such as sodium pentosan polysulfate, calcium pentosan polysulfate, or potassium pentosan polysulfate, for example. Pentosan may be obtained naturally from plants, microorganisms, or synthesized. Accordingly, references to pentosan polysulfate throughout this application may refer to pentosan polysulfate as well as to the various salts thereof, as appropriate whether obtained naturally, synthetically or semi-synthetically.

Pentosan polysulfate according to the present invention, is available as an alkali metal salt or alkaline earth metal salt, for example, comprising calcium or sodium salt, or transition metals such as copper and zinc and noble metals such as platinum. Accordingly, the particular complexing ions may be selected from the group consisting of the alkali metals, e.g. $Na^+$ and $K^+$, alkaline earth metals, e.g. $Ca^{2+}$, $Zn^{2+}$, $Mg^{2+}$, $Ba^{2+}$ as well as $Ag^+$, $Pb^{2+}$, $Cu^{2+}$, $Au^{2+}$, $Pd^{2+}$, $Pd^{4+}$, $Pd^{4+}$, $Pd^{2+}$, trivalent metal ions, and quaternary ammonium compound complexes. Examples of the latter compound are pyridinium chloride, tetraalkyl ammonium chloride, chorine chloride, cetylpyridinium chloride, N-cetyl-N,N,N-trialkylammonium chloride or their derivatives. The most preferred of these are the divalent alkaline earth metals, preferably calcium, and magnesium and most preferable is the calcium complex. Preparation of the polysulfate polysaccharide-metal complexes is described in detail in U.S. Pat. No. 5,668,116; see also U.S. Patent Publication No. 2009/0111771 to Cullis-hill et al., which are hereby incorporated by reference in their entirety.

This third aspect is carried out in accordance with the previously described aspects. Modes of administration and therapeutically effective dosing related to this aspect of the invention are described supra.

A fourth aspect of the present invention relates to a method of treating a subject with a skeletal pathology associated with a lysosomal storage disorder. The method includes selecting a subject with a skeletal pathology associated with a lysosomal storage disorder and administering to the selected subject an agent for substrate reduction therapy and an agent for an anti-TNF-α treatment under conditions effective to treat the lysosomal storage disorder in the subject.

Substrate reduction therapy, as defined herein, is a therapeutic approach which aims to reduce the synthesis of the substances in the cell and thereby provide equilibrium with a reduced enzyme activity available in lysosomal storage diseases.

Zavesca® (miglustat), a substrate reduction therapy, has now been approved in the United States and European countries for Gaucher disease, and has potential for treating other lysosomal storage diseases in the same metabolic pathway. Cystagon® (cysteamine) has also been investigated as a substrate reduction therapy for infantile neuronal ceroid lipofuscinosis. Zavesca and Cystagon are small molecules that are believed to pass the blood-brain barrier. This type of therapy is applicable for those patients with some residual enzyme activity, and it requires a fine balance with the synthesis and catabolizing processes (U.S. Patent Publ. No. 2005/0208090 to Keimel, et al., which is hereby incorporated by reference in its entirety). In one embodiment, the agent for substrate reduction therapy is Miglustat or Eliglustat.

In one embodiment, an additional therapy is administered in accordance with the previous aspects, but the additional therapy may also be enzyme replacement therapy, as described supra.

This fourth aspect is carried out in accordance with the previously described aspects. Modes of administration and therapeutically effective dosing related to this aspect of the invention are described supra.

Having now generally described the invention, the same will be more readily understood through reference to the following examples which are provided by way of illustration, and are not intended to be limiting of the present invention, unless specified.

EXAMPLES

The following examples are provided to illustrate embodiments of the present invention but are by no means intended to limit its scope.

Example 1

Materials and Methods

Animals—

The MPS VI rats have been previously described and used extensively by the researchers of the present invention and others (Yoshida et al., "Arylsulfatase B-Deficient Mucopolysaccharidosis in Rats," *J. Clin. Invest.* 91:1099-1104 (1993); Kunieda et al., "Mucopolysaccharidosis Type VI in Rats: Isolation of cDNAs Encoding Arylsulfatase B, Chromosomal Localization of the Gene, and Identification of the Mutation," *Genomics* 29:582-587 (1995), both of which are hereby incorporated by reference in their entirety). A breeding colony was established from heterozygous mating pairs, and genotyping was performed on tail clip DNA using established methods (Kunieda et al., "Mucopolysaccharidosis Type VI in Rats: Isolation of cDNAs Encoding Arylsulfatase B, Chromosomal Localization of the Gene, and Identification of the Mutation," *Genomics* 29:582-587 (1995), which is hereby incorporated by reference in its entirety). Euthanasia of rats was performed using carbon dioxide inhalation. All animal protocols were approved by the Mount Sinai Institutional Animal Care and Use Committee (permit #08-0108), and were performed in accordance with NIH guidelines.

Treatment of MPS VI Rats—

Naglazyme® (recombinant human N-acetylgalactosamine-4-sulfatase) was obtained from the BioMarin Pharmaceutical Inc., and CNTO1081 was from Centocor Ortho Biotech Inc. Twenty one-day-old (pre-symptomatic) MPS VI rats were divided into two groups (n=8/group), and subjected to either ERT or combined ERT/anti-TNF-α therapy. Animals receiving ERT alone were injected i.v. (tail vein) weekly with 1 mg/kg of Naglazyme®. Those receiving combined therapy also were injected i.v. with 3 mg/kg of CNTO10181 twice per week (every third day). Treatment was carried out for a total of 32 weeks. Serum was collected every 2 weeks for TNF-α and RANKL analysis (see infra). For each group, the treated animals were sacrificed 2 weeks after the last injection (37 weeks of age). Age-matched normal and untreated MPS VI rats were used as controls throughout the study.

Tracheas, femora, and tibias were collected from the control and treated MPS VI rats, and placed in either phosphate buffered saline for the isolation of fibroblast-like synoviocytes (FLS) and articular chondrocytes, or fixed in neutral buffered 10% formalin (Sigma Chemical) for histology, microCT analysis, and immunohistochemistry (see infra). The fixed bones were decalcified in 8% formic acid (Sigma Chemical) for 5 days, paraffin embedded, and sectioned (5 μm) for subsequent staining Primary FLS and articular chondrocyte cultures were established as previously described (Simonaro et al., "Joint and Bone Disease in Mucopolysaccharidosis VI and VII: Identification of New Therapeutic Targets and Biomarkers Using Animal Models," *Pediatr. Res.* 57:701-707 (2005); Simonaro et al., "Mechanism of Glycosaminoglycan-Mediated Bone & Joint Disease: Implications for the Mucopolysaccharidoses & Other Connective Tissue Diseases," *Amer. J. Path.* 172:112-122 (2008), both of which are hereby incorporated by reference in their entirety), and expression of inflammatory and apoptosis markers were assessed by western blotting.

MicroCT Image Acquisition—

Three-dimensional images of the 37-week-old femora from age-matched normal, untreated and treated MPS VI rats were obtained using the eXplore Locus SP PreClinical Specimen microCT system (GE Healthcare; London, Ontario, Canada). Scans were performed at a voxel size of 14.4 μm. The scan protocol consisted of 3600 image acquisitions over a five hour scan (acquisition parameters: 80 kVp, 80 uA, 3 second exposure time [~690], 0.010" aluminum beam filter). A calibration phantom containing air, water, and hydroxyapatite (SB3: Gamex RMI, Middleton, Wis., USA) was included in all scans to adjust for the variability in X-ray attenuation inherent to independent scan sessions.

Bone Length and Trachea Measurements—

Limb and trachea measurements were taken at the end of the study (37 weeks of age). The length of each femur was measured from the microCT images using the Microview software. The greater trochanter was used as the proximal margin of the femur, whereas the extent of the distal condyles was considered the distal margin. Thus, the length of each femur was computed roughly along the vertical axis of the bone. For validation, the physical femora and tibia lengths, as well as the width of the tracheas, was measured with a digital caliper. The mean of the two treatment groups (ERT and combined ERT/CNTO1081) were compared using standard student t test analysis.

Cortical Bone Analysis—

A representative mid-diaphyseal region of each femoral microCT image was isolated for analysis. The volume of interest (VOI) was limited proximally by the initial appearance of the third trochanter and distally by the appearance of the metaphysis, indicated by trabecular bone formation and shaft width expansion. The analysis region was not restricted by measured size to accommodate variances in bone length. Cortical bone was manually segmented from residual trabecular bone and thresholded independently to differentiate bone and non-bone voxels. The MicroView software was employed to quantify morphological traits.

The microCT images were further processed to quantify the tissue mineral density (TMD) of cortical bone within each sample. TMD represents the average mineral value of the bone voxels only, expressed in hydroxyapatite (HA) density equivalents, in contrast to the bone mineral density (BMD), which includes non-bone voxels. TMD was calculated by converting the gray-scale values of bone voxels from Hounsfield units (HU) to mineral values (mg/cc of HA) through the use of a calibration phantom containing air, water, and HA (Gamex RMI, Middleton, Wis., USA). TMD is defined as the average bone voxel HU value divided by the average HU value of the HA phantom multiplied by 1130 mg/cc (density of HA).

Trabecular Bone Analysis—

Trabecular VOIs were extracted from a 4 mm region of the distal metaphysis of the femur using the MicroView image processing software. The distal margin was defined as the initial appearance of the physis. In lieu of an obvious proximal landmark, a standard distance (4 mm) was selected to encompass the trabecular VOI. Trabecular bone was segmented from the cortical bone in serial axial slices to generate a three dimensional representation of the trabecular VOI. Each trabecular VOI was thresholded to distinguish bone from non-bone voxels. The TMD of trabecular bone was computed from the microCT scan in the same fashion as for cortical bone, with the inclusion of the same calibration phantom in each scan. Microarchitectural traits were measured using the Microview software, including trabecular bone volume fraction, trabecular bone surface-to-volume ratio, and trabecular number, thickness, and spacing. All values were averaged across the entire VOI.

Locomotor Function—

Age-matched 37-week-old normal and untreated MPS VI and treated MPS VI rats were placed on an accelerating Rotarod series 8 (IITC Life Science) for evaluation as described previously (Cotugno et al., "Different Serum Enzyme Levels are Required to Rescue the Various Systemic Features of the Mucopolysaccharidoses," *Hum. Gene Ther.* 21:555-69 (2010), which is hereby incorporated by reference in its entirety). Animals were primed on the rod for two consecutive days prior to the actual recording. The rotarod was set at increasing speeds from 10 to 30 rpm over 3 minutes, and an average of the latency to fall off from the rod was recorded. Results were analyzed by one-way analysis of variance (ANOVA) with the variable group.

Motility Analysis—

The fore and hind paws of treated and control animals were stained with two different colors using non-toxic dye. The rats were trained to walk through a tunnel for two consecutive days, leaving their paw prints on blotting paper. On the third day several parameters were measured; distance between the left and right front paws in the longitudinal direction, the angle that was formed, and the distance between the front and hind right paws. For statistical analysis, group differences were assessed using multivariate analyses of variance (MANOVAs), followed by post hoc Bonferroni adjustments for all time points tested.

Articular Cartilage, Synovium and Growth Plate Histology and Immunohistochemistry—

Femora from 37-week-old normal, untreated MPS VI and treated MPS VI rats were fixed, embedded, sectioned, and stained with toluidine blue and H & E. Immunohistochemical studies were performed as well. For immunohistochemistry, sections were fixed with 4% paraformaldehyde/PBS, permeabilized with 0.5% Triton-X-100, blocked, and incubated overnight at 4° C. with primary rabbit polyclonal anti-mouse collagen type IIA1 (rabbit polyclonal sc-28887, Santa Cruz Biotechnology) and TNF-α antibody (goat polyclonal sc-1348, Santa Cruz Biotechnology). After several rinses with PBS, visualization was accomplished using a fluorescent secondary antibody, donkey anti-goat IgG-Cy-3 (711-165-152, Jackson Laboratory). Nuclei were stained with 1 mg/ml bis-benzimide Hoechst dye (Sigma-Aldrich) for 10 min, rinsed, and sections were mounted with an anti-bleaching mounting media. Slides were visualized and photographed with a confocal laser-scanning microscope (Carl Zeiss 510 Meta).

Trachea Immunohistochemistry—

Tracheas from 37-week-old normal, untreated MPS VI and treated MPS VI rats were fixed, embedded, sectioned, and prepared as described above. Sections were incubated overnight with primary mouse monoclonal anti-ceramide antibody (MID 15B4, Alexis Corporation) and visualization was accomplished using a fluorescent secondary antibody, donkey anti-goat IgG-Cy-3 (711-165-152, Jackson Laboratory). Slides were visualized and photographed with a confocal laser-scanning microscope (Carl Zeiss 510 Meta).

Immunoblot Analysis—

Articular chondrocytes from 37-week-old normal, untreated and treated MPS VI rats were collected using sequential enzyme digestion of cartilage, pelleted and lysed for immunoblot analysis as previously described (Simonaro et al., "Mechanism of Glycosaminoglycan-Mediated Bone & Joint Disease: Implications for the Mucopolysaccharidoses & Other Connective Tissue Diseases," Amer. J. Path. 172: 112-122 (2008), which is hereby incorporated by reference in its entirety). The membranes were incubated with rabbit polyclonal anti-collagen type IIA1 (sc-8784-R, Santa Cruz Biotechnology), rabbit polyclonal anti-collagen type X (AB58632, Abcam), rabbit polyclonal anti-ADAMTS5 (sc-28887, Santa Cruz Biotechnology), rabbit polyclonal anti-PARP (sc-7150, Santa Cruz Biotechnology), and rabbit polyclonal anti-GAPDH (sc-25778, Santa Cruz Biotechnology), as a loading control. The bound antibodies were recognized by secondary antibodies conjugated to HRP (NA934V), GE Healthcare). Detection of the antibody complexes was accomplished using an enhanced chemiluminescence detection reagent (Amersham Biosciences).

Serum Immunoassays—

Serum TNF-α and RANKL in age-matched normal, untreated and treated MPS VI rats were assessed by immunoassays using rat ultrasensitive Biosource Elisa kits (Invitrogen and ALPCO Diagnostics) according to the manufacturers' protocols. All assays were performed in triplicate.

Data Presentation and Statistical Analyses—

All experiments were independently replicated at least three times. The data between two groups were subjected to student's t-test analysis, one-way analysis of variance (ANOVA) with the variable group, multivariate analyses of variance (MANOVAs) followed by post hoc Bonferroni adjustments. The results were considered significant at P<0.05. Statistics were performed using Sigma Stat 3.1 (Systat Software). Graphs represent the mean+/−standard error of the mean (SEM) of combined data from the triplicate experiments.

Example 2

Effect of Anti-TNF-α Therapy on Enzyme Replacement Therapy in the Mucopolysaccharidoses Twenty one-day-old MPS VI rats were treated by either ERT (1 mg/kg once per week), or by a combined protocol of ERT and anti-TNF-α therapy (3 mg/kg, twice per week). Both were administered intravenously (tail vein). The animals were treated for a total of 8 months (i.e., 32 doses of ERT and 64 doses of anti-TNF-α). As controls, normal and untreated MPS VI littermates were used (n=8 per group). Anti-TNF-α therapy was carried out using a rat-specific monoclonal antibody against TNF-α CNTO1081 (gift of Centocor). Naglazyme® (gift of BioMarin) is the human form of recombinant N-acetylgalactosamine-4-sulfatase, the enzyme deficient in MPS VI, and was used for ERT. The animals were sacrificed 2 weeks after the final treatment (i.e., 37 weeks-of-age).

FIG. 1A summarizes the serum levels of TNF-α and RANKL at the end of the study. Both inflammatory markers were highly elevated in untreated MPS VI rats as compared to normal animals, and both treatment protocols led to significant reductions. The effects were slightly enhanced in the combined treatment group, although not statistically different. FIG. 1B shows immunohistochemical staining of articular cartilage for TNF-α. Untreated MPS VI animals had elevated cartilage TNF-α, which was modestly reduced by ERT and more so by combined treatment. FIG. 1C shows cross sectional images of the knees from control and treated MPS VI rats. The synovial membranes (*) were hyperplastic in untreated MPS VI rats, leading to the formation of synovial villi (SV). ERT did not reduce the synovial inflammation, in contrast to combined treatment where the inflammation and formation of villi was markedly reduced. Note that storage was still clearly evident in the articular cartilage (AC) from both treatment groups, as well as in the subchondral bone (SB). The bold arrowhead in the ERT image indicates the invasion of the synovial membrane into the SB, indicative of inflammation.

Example 3

Figure 2A:
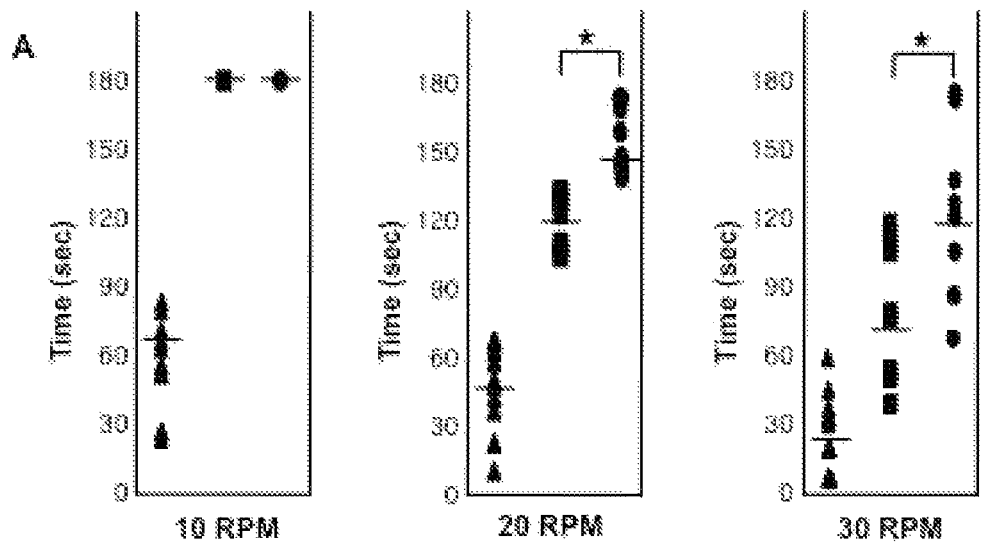
FIGS. 2A-2B show motor activity and gait analysis in untreated and treated MPS VI rats.
Figure 2B:
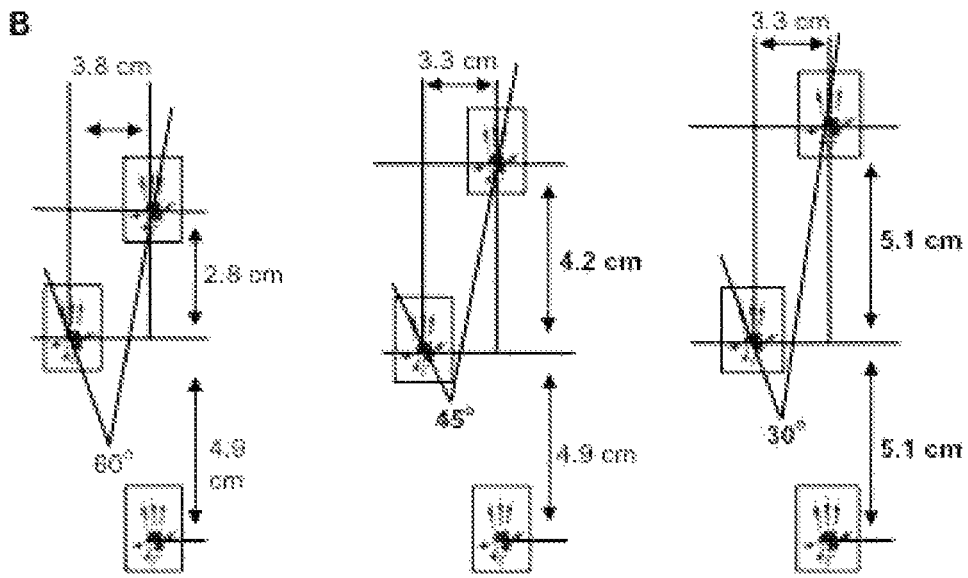

Effect of Enzyme Replacement Therapy and Anti-TNF-α Therapy on Motor Activity, Gait, Bone Disease, and Joint Disease The effects of these treatments on motor activity and gait also were evaluated. On an accelerating rotarod apparatus (FIG. 2A), both the ERT and combined treatment animals remained on the rotating bar for the maximum time (180 seconds) at the lowest speed (10 RPM), in contrast to untreated MPS VI animals (mean of 70 seconds). At higher speeds (20 and 30 RPM), a significant improvement in the combined treatment versus ERT group was observed. FIG. 2B shows representative images of the gait patterns for these animals. Overall, the ERT treated animals walked faster with longer, more coordinated strides than the untreated MPS VI animals, and this was improved by combined therapy. For example, the angle of the hind paw movement reduced from 60° (untreated MPS VI), to 45° (ERT) to 30° (combined), and the distance for the front paw improved from 2.8 cm (untreated) to 4.2 cm (ERT) to 5.1 cm (combined).

Figures 3A, 3B, 3C:
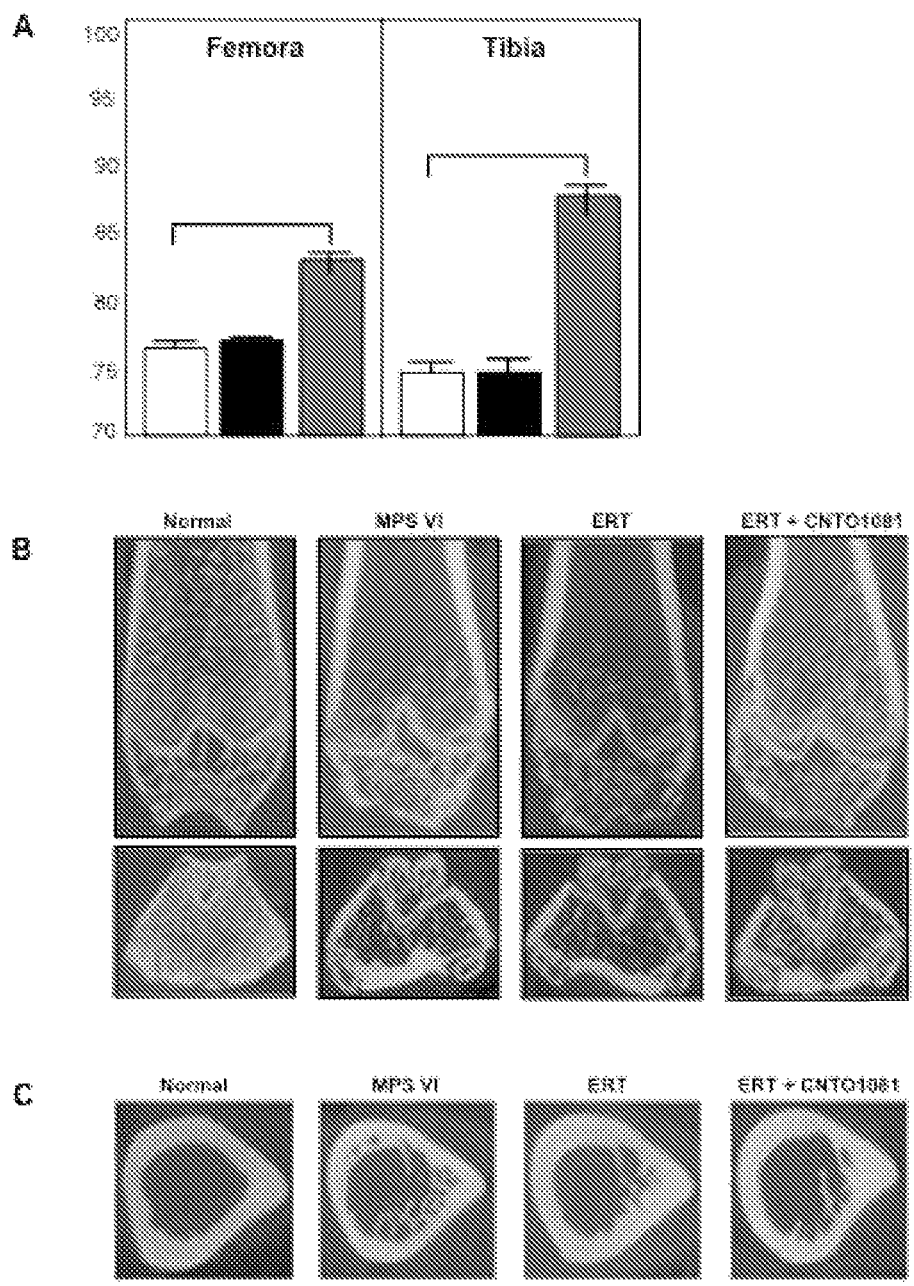
FIGS. 3A-3C show bone length and micro-architecture in untreated and treated MPS VI rats.

MicroCT analysis was used to assess the femur and tibia lengths in the treated and untreated MPS VI, and normal animals. As shown in FIG. 3A, at 37 weeks-of-age the femora of untreated MPS VI animals were on average only approximately 77% those of normal littermates. No improvements were observed in the ERT group, while in the animals receiving the combined treatment the femora were approximately 6% longer (approximately 83% of normal). The tibias of untreated MPS VI rats were similarly approximately 74% of normal, and these were improved approximately 14% by combined therapy, to approximately 88% of normal. No improvement was observed in the ERT group. Although these improvements in bone length from the combined treatment were consistently observed, they were more prominent in male animals and did not reach statistical significance when all of the treated mice (male and female) were grouped together.

Despite these positive effects on bone length, few changes were evident in the bone micro architecture for either treatment group. FIGS. 3B and 3C show microCT images of the distal femora. In untreated MPS VI animals the trabecular density within the metaphyseal bone was reduced, the physeal growth plate was dysmorphic and disrupted, and the epiphyseal trabeculae were disorganized relative to the normal femur (FIG. 3B). Mild improvements from the combined treatment were detected.

Quantitative analysis was conducted to further investigate the morphological changes in trabecular bone of untreated and treated MPS VI rats. Representative volume of interests (VOIs) of the distal metaphysis, immediately proximal to the physis, were gathered and compared across groups. Three-dimensional images of trabecular structures were generated to ensure only trabecular bone was included. From each VOI, the TMD (trabecular mineral density) and BV (bone volume)/TV (trabecular volume) were extracted. Neither treatment protocol had a statistically relevant impact on trabecular bone TMD or BV/TV.

MicroCT images of the mid-diaphyseal region of the femora also were collected. Axial cross-sections at the distal appearance of the third trochanter were extracted and representative samples juxtaposed for comparison (FIG. 3C). On gross inspection, untreated MPS VI rats exhibited greater subcortical trabecular infiltration into the marrow space. The apparent increase in trabecular density was not corroborated by quantitative measures, although this gross finding was consistent across the range of samples. No marked reversal of the trabecular growth resulted from either treatment.

Quantitative measures of cortical bone morphology were calculated for the mid-diaphyseal VOIs. Values for the mean cross-sectional cortical area, total area, and TMD of cortical bone were gathered to illustrate size and mineralization. Cortical area was 22% ($p=0.002$) lower in MPS VI rats compared to normal, without influencing the total area or TMD. As a result, the relative cortical area was depressed by 15% ($p=0.015$), representing a substantial loss of cortical bone thickness in MPS VI rats at no expense to the total thickness or mineralization of diaphyseal femoral bone. Of note, femora of rats treated with ERT or combined treatment exhibited greater cortical area and relative cortical area, without a significant change in the total area or TMD. The addition of anti-TNF-α therapy did not augment the positive effect of ERT therapy. Overall, these findings fell short of statistical significance.

Robustness was calculated as a final measure of femoral architecture. Defined as the cross-sectional size relative to length, robustness captures the relationship between horizontal and vertical growth. MPS VI femurs were found to be more robust than normal, consistent with their "short and fat" appearance. No significant improvement was demonstrated with treatment, although the combined therapy reduced robustness by 5% ($p=0.25$), a modest (albeit insignificant) improvement.

Collapsed and thickened tracheas were evident in the untreated MPS VI rats (FIG. 4A), consistent with the tracheal abnormalities observed in MPS patients (Semenza et al., "Respiratory Complications of Mucopolysaccharide Storage Disorders," *Medicine* 67:209-19 (1988), which is hereby incorporated by reference in its entirety). Upon gross inspection, a notable improvement of the tracheas was observed following combined treatment, but not ERT. Tracheas from untreated MPS VI rats had a statistically smaller cross-sectional area when compared to normal (2.9±0.6 mm$^2$ versus 7.5±0.8 mm$^2$; $p=0.0002$). Tracheas from ERT treated animals were modestly, but significantly, improved (3.6±0.5 mm$^2$; $p=0.02$ compared to untreated), while in the combined treatment group the cross-sectional areas were nearly doubled, 6.0±0.8 mm$^2$ ($p=0.003$ compared to untreated).

Example 4

Ceramide Staining in Mucopolysaccharidoses Articular Chondrocytes

Figures 4A, 4B:
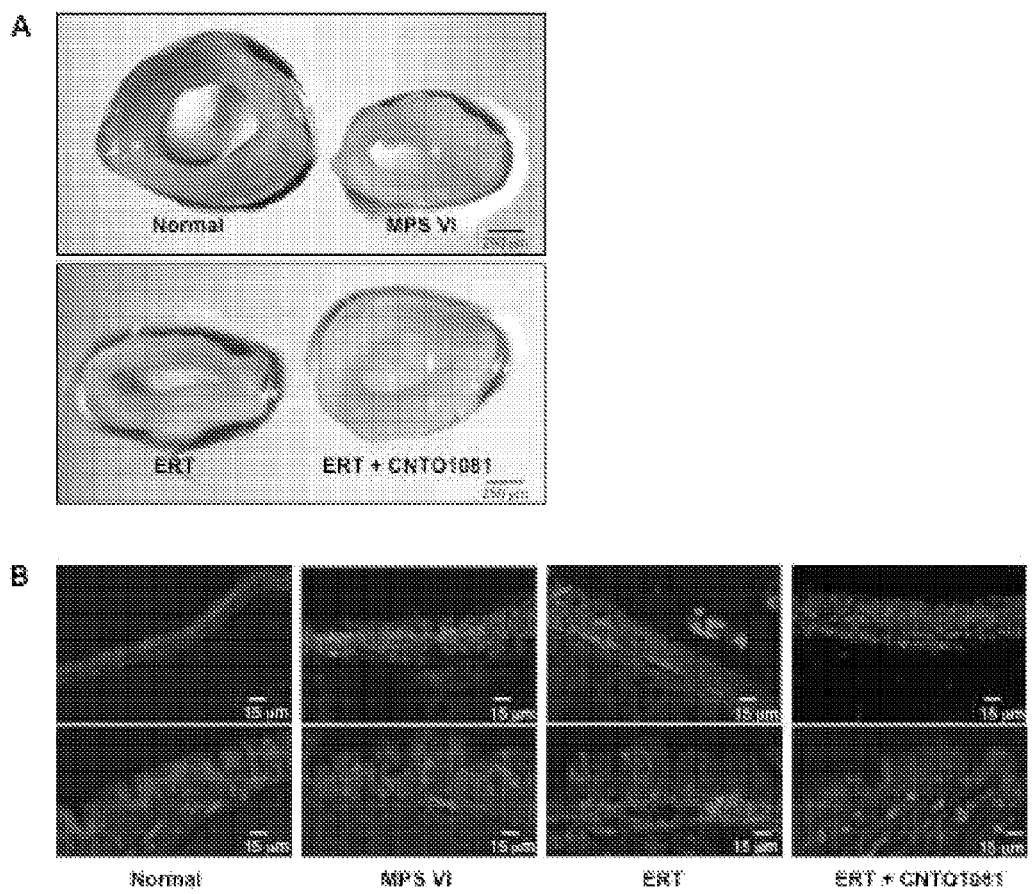
FIGS. 4A-4B illustrate tracheal defects in untreated and treated MPS VI rats.

Ceramide is a signaling sphingolipid that is involved in the induction of inflammation, apoptosis, and infection, and has been shown to accumulate in MPS articular chondrocytes (Simonaro et al., "Involvement of the Toll-Like Receptor 4 Pathway and Use of TNF-Alpha Antagonists for Treatment of the Mucopolysaccharidoses," *Proc. Natl. Acad. Sci.* 107:222-7 (2010), which is hereby incorporated by reference in its entirety). Ceramide also accumulates in the trachea from several diseases with respiratory complications, and plays an important role in cartilage homeostasis (Becker et al., "Accumulation of Ceramide in the Trachea and Intestine of Cystic Fibrosis Mice Causes Inflammation and Cell Death," *Biochem. Biophys. Res. Commun.* 17:368-74 (2010), which is hereby incorporated by reference in its entirety), leading to the examination of ceramide in the tracheas of the MPS VI rats. As seen in FIG. 4B, strong ceramide staining was observed in the epithelial cells of untreated and ERT-treated MPS VI rat tracheas, and was reduced to normal in tracheas from animals receiving combined treatment.

Example 5

Histological Analysis of Bone Growth Plates

To examine the effects of these therapies further, histological analysis of the bone growth plates was performed. MPS VI rat growth plates are thicker than those of wild-type littermates due to the large, vacuolated cells. In addition, the normal column organization of the growth plates is disrupted in the MPS animals, contributing to the abnormal bone formation (Simonaro et al., "Involvement of the Toll-Like Receptor 4 Pathway and Use of TNF-Alpha Antagonists for Treatment of the Mucopolysaccharidoses," *Proc. Natl. Acad. Sci.* 107:222-7 (2010); Metcalf et al., "Mechanism of Shortened Bones in Mucopolysaccharidosis VII," *Mol. Genet. Metab.* 97:202-211 (2009), both of which are hereby incorporated by reference in their entirety). Neither treatment protocol had a noticeable effect on the MPS VI growth plate histology.

Example 6

Collagen Expression in Articular Chondrocytes

Figure 5A:
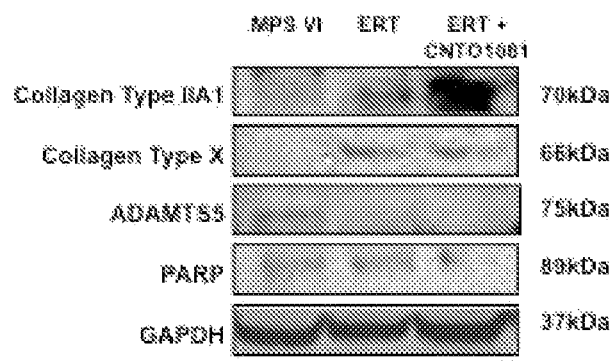
FIGS. 5A-5B show protein expression in articular chondrocytes from untreated and treated MPS VI rats.
Figure 5B:
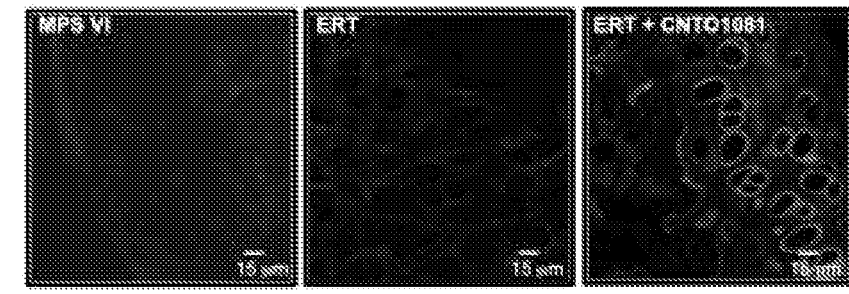
Figures 6A, 6B, 6C, 6D:
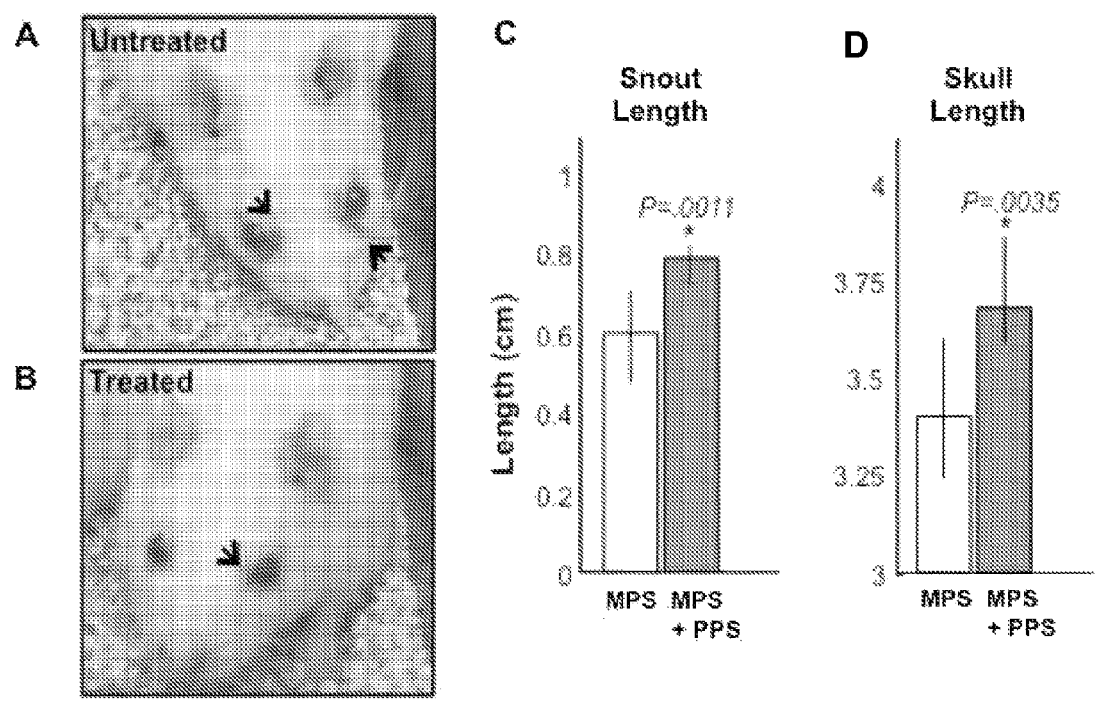
FIGS. 6A-6D show results of MPS VI rats treated with PPS. MPS VI rats were maintained on normal watering (FIG. 6A) or with water containing 25 mg/day PPS (n=6/group) (FIG. 6B). Animals were 6 months of age when treatment began, and treatment was carried out for 3 months. Skull and snout images were taken at the end of treatment. Representative images are shown. Snout length is shown in FIG. 6C, while skull length is shown in FIG. 6D. Skull length and width measurements also were determined from the radiographs for each of the animals, and the data are shown in the bar graph (FIGS. 6C, 6D). White=normal 9 month old, Gray=MPS VI rats on normal water; Blue=MPS VI rats receiving PPS. *=$p<0.01$.

Finally, articular chondrocytes were collected from treated and untreated MPS VI animals to assess changes in collagen expression and apoptosis markers. The levels of collagen IIA1 and X are lower than normal in MPS VI rats, and each was elevated in the treated versus untreated MPS VI animals (FIG. 5A). As evident in this western blot, combined treatment led to greater collagen IIA1 expression, a finding that was confirmed by immunohistological staining in cartilage slices (FIG. 5B). This is consistent with previous work showing that anti-TNF-α therapy reduced TUNEL staining in articular chondrocytes of the MPS VI rats (Simonaro et al., "Involvement of the Toll-Like Receptor 4 Pathway and Use of TNF-Alpha Antagonists for Treatment of the Mucopolysaccharidoses," *Proc. Natl. Acad. Sci.* 107:222-7 (2010), which is hereby incorporated by reference in its entirety). Expression of the matrix-degrading enzyme, aggrecanase, ADAMTS5, was reduced by both ERT and combined treatment, while the apoptosis marker, PARP, which is elevated in chondrocytes from MPS VI rats (Simonaro et al., "Articular Chondrocytes From Animals With a Dermatan Sulfate Storage Disease Undergo a High Rate of Apoptosis and Release Nitric Oxide and Inflammatory Cytokines: A Possible Mechanism Underlying Degenerative Joint Disease in the Mucopolysaccharidoses," *Lab Investi.* 81:1319-1328 (2001), which is hereby incorporated by reference in its entirety), was only reduced by the combined treatment protocol.

Example 7

Effects of Enzyme Replacement Therapy in the Mucopolysaccharidoses

Despite the fact that ERT provides clear clinical benefits to MPS patients, including improved joint mobility, motility and breathing (Decker et al., "Enzyme Replacement Therapy for Mucopolysaccharidosis VI: Growth and Pubertal Development in Patients Treated With Recombinant Human N-Acetylgalactosamine 4-Sulfatase," *J. Pediatr. Rehabil. Med.* 3:89-100 (2010); Miebach, E, "Enzyme Replacement Therapy in Mucopolysaccharidosis Type I. Treatment of Mucopolysaccharidosis Type II (Hunter syndrome) with Idursulfase: The Relevance of Clinical Trial End Points," *Acta Paediatr. Suppl.* 94:58-60 (2005), both of which are hereby incorporated by reference in their entirety), the effectiveness of this treatment on cartilage and bone are extremely limited. This may be attributed to the biodistribution of the infused recombinant enzymes, which cannot readily reach these tissues due to their poor vascular supply, and the fact that the target cells (e.g., chondrocytes) are embedded within a matrix that impedes drug delivery. The improved joint mobility in MPS patients following ERT is therefore thought to relate to soft tissue changes (e.g., tendons), rather than direct effects on cartilage and bone. In addition, even when the recombinant enzymes have been injected directly into the articular space of MPS animals at very early ages, the effects on the bone and cartilage have been very limited (Auclair et al., "Long-Term Intra-Articular Administration of Recombinant Human N-Acetylgalactosamine 4-Sulfatase in Feline Mucopolysaccharidosis VI," *Mol. Gen. Metab.* 91:352 (2007), which is hereby incorporated by reference in its entirety). Thus, there remains an important need to improve the outcome of ERT in these tissues.

Example 8

Effects of Anti-TNF-α Therapy in the Mucopolysaccharidoses

Previous work by applicant has demonstrated the importance of the TLR4 inflammatory pathway in the pathogenesis of cartilage and bone in MPS animal models (Simonaro et al., "Involvement of the Toll-Like Receptor 4 Pathway and Use of TNF-Alpha Antagonists for Treatment of the Mucopolysaccharidoses," *Proc. Natl. Acad. Sci.* 107:222-7 (2010), which is hereby incorporated by reference in its entirety). Since no direct TLR4 inhibitors are approved for clinical use, the effectiveness of anti-TNF-α therapy was evaluated with a downstream product of the TLR4 pathway in the rat model of MPS VI. In humans, anti-TNF-α antibodies (e.g., Remicade® (infliximab)) are used to treat several common inflammatory diseases, including rheumatoid arthritis, psoriatic arthritis, and Crohn's disease (Klaasen et al., "Body Mass Index and Clinical Response to Infliximab in Rheumatoid Arthritis," *Arthritis Rheum.* 63:359-64 (2011); Rodgers et al., "Etanercept, Infliximab and Adalimumab for the Treatment of Psoriatic Arthritis: A Systematic Review and Economic Evaluation," *Health Technol. Assess.* 15:1-329 (2011); Rutella et al., "Infliximab Therapy Inhibits Inflammation-Induced Angiogenesis in the Mucosa of Patients With Crohn's Disease," *Am. J. Gastroenterol.* (2011), all of which are hereby incorporated by reference in their entirety). It was found that treatment of MPS VI rats by this anti-TNF-α therapy reduced inflammation and articular cartilage apoptosis, but did not significantly improve bone growth or mobility (Simonaro et al., "Involvement of the Toll-Like Receptor 4 Pathway and Use of TNF-Alpha Antagonists for Treatment of the Mucopolysaccharidoses," *Proc. Natl. Acad. Sci.* 107:222-7 (2010), which is hereby incorporated by reference in its entirety).

Example 9

Effects of Combined Enzyme Replacement Therapy and Anti-TNF-α Therapy in the Mucopolysaccharidoses In the current study the effectiveness of combining ERT with anti-TNF-α therapy was evaluated to determine if there was any clinical/pathological benefit over ERT alone. A rat-specific monoclonal antibody was used against TNF-α (CNTO1081), and the human recombinant N-acetyl-galactosamine-4-sulfatase (Naglazyme®) for ERT. Immune responses against this human enzyme are known to occur in MPS VI rats and cats after intravenous injections, although these reactions are generally not severe. Immunosuppression can be used to minimize this response (Connor, V, "Anti-TNF Therapies: A Comprehensive Analysis of Adverse Effects Associated With Immunosuppression," *Rheumatol. Int.* 31:327-37 (2011), which is hereby incorporated by reference in its entirety), but since anti-TNF-α therapy was already administered in this study, a known immunosuppressant, an additional complex treatment was not added to the experimental design of the present invention. For some ERT therapies immunological responses to the infused enzymes may seriously limit their effectiveness, and one potential benefit of combining anti-TNF-α therapy with ERT may be to minimize this response and avoid the need for additional immunosuppression. However, this potential benefit must be carefully balanced with the potential risk of increased infection, and therefore carefully evaluated in controlled clinical trials.

Interestingly, one of the initial observations from the current study was that ERT alone substantially reduced the serum levels of several inflammatory markers, including TNF-α and RANKL. The serum levels of these cytokines reflects the overall inflammatory state of these animals, rather than any specific organ or tissue, and it was hypothesized that the reduction in the circulating levels of these molecules following ERT was likely due to the effectiveness of the therapy in organs known to be readily assessable to the recombinant enzyme (e.g., liver). It has previously been shown that the inflammatory disease in MPS is driven, in large part, by GAG storage, and a reduction of GAGs in these organs following ERT may have led to reduced systemic TNF-α release (Simonaro et al., "Involvement of the Toll-Like Receptor 4 Pathway and Use of TNF-Alpha Antagonists for Treatment of the Mucopolysaccharidoses," *Proc. Natl. Acad. Sci.* 107:222-7 (2010), which is hereby incorporated by reference in its entirety). The fact that the circulating levels of TNF-α (and other inflammatory molecules) was substantially reduced in these animals following ERT also suggests that this therapy might have positive, secondary anti-inflammatory effects on other organs that are not accessible to the enzyme (e.g., cartilage), providing additional benefit. Throughout the course of enzyme replacement therapy treatment for lysosomal storage disorder patients, serum markers of inflammation, toxicity, etc., are routinely measured. See Simonaro et al., "Involvement of the Toll-Like Receptor 4 Pathway and Use of TNF-Alpha Antagonists for Treatment of the Mucopolysaccharidoses," *Proc. Natl. Acad. Sci.* 107:222-7 (2010), which is hereby incorporated by reference in its entirety. MPS patients subjected to enzyme replacement therapy may be expected to have normal or near normal levels of TNF-α. Based on the cytokine serum results, it would have appeared that enzyme replacement therapy alone was effective. As such, experts in the field who treat lysosomal storage disorder patients with enzyme replacement therapy would not have considered adding TNF-α onto the treatment regime prior to the results of the present invention.

The clinical improvement in the treated MPS VI animals was assessed by two measures of motor activity, performance on an accelerating rotarod apparatus and gait analysis. ERT improved these endpoints, but there was a clear, additive benefit of combining this therapy with anti-TNF-α treatment. It was hypothesized that the positive effects of ERT on these phenotypes were likely due to soft tissue changes in the joints, rather than direct delivery of the enzyme to the cartilage or bone. Since the MPS VI rats do not exhibit markedly enlarged livers and spleens, the improved motor activity and gait following ERT also cannot be attributed to reduced organ size, although clearly this is a positive benefit in MPS patients treated by ERT.

Importantly, the additive benefits of combined ERT/CTN01018 treatment on these clinical endpoints were significant, and occurred despite the fact that the reduction of serum TNF-α and RANKL in both treatment groups were similar. Indeed, several changes were observed in the cartilage of the animals receiving combined treatment that were not observed in the ERT group. For example, the tracheas of MPS VI rats receiving combined therapy were significantly thinner and wider than untreated or ERT-treated animals, and collagen IIA1 expression was elevated in the articular collagen. Ceramide also was reduced in the tracheas, indicative of reduced inflammation, and PARP expression (indicative of apoptosis) was reduced in articular chondrocytes.

In addition, inflammation of the synovium was markedly reduced by the combined therapy, resulting in fewer villi and less invasion of the synovial tissue into the underlying bone. Whether these changes were due to a direct effect of CTN01018 on these tissues, or an indirect effect resulting from systemic reduction of TNF-α, remains unknown. The effects on tracheal morphology were particularly notable, suggesting that the respiratory complications associated with the tracheal pathology in MPS patients may benefit from the positive effects of combined ERT/anti-TNF-α therapy (Semenza et al., "Respiratory Complications of Mucopolysaccharide Storage Disorders," *Medicine* 67:209-19 (1988); Shinhar et al., "Airway Management in Mucopolysaccharide Storage Disorders," *Arch. Otolaryngol. Head Neck Surg.* 130: 233-237 (2004), both of which are hereby incorporated by reference in their entirety). CTN01018 is an antibody against TNF-α. As such, it has a molecular weight and biodistribution that would not have been expected to reach the primarily avascular cartilage tissues such as the trachea.

Despite these positive changes in the joints and tracheas of the treated MPS VI animals, there were few effects evident in the bones. Femora and tibia lengths were mildly improved by the combined treatment, but the growth plate histology was not. These changes in bone length were very modest compared to those previously observed in MPSVII/TLR4 double knockout animals (Simonaro et al., "Involvement of the Toll-Like Receptor 4 Pathway and Use of TNF-Alpha Antagonists for Treatment of the Mucopolysaccharidoses," *Proc. Natl. Acad. Sci.* 107:222-7 (2010), which is hereby incorporated by reference in its entirety), where a clear improvement in the growth plate organization was evident along with significantly longer bones. However, several important differences between the two experiments should be recognized, including different rodent models and diseases, and the fact that in the MPS VII mouse study created a complete knockout of the TLR4 pathway that was exhibited throughout development, while in the current study the rats were subjected to treatment with a systemic anti-TNF-α therapy beginning at approximately 3 weeks.

Overall, these results suggest that combining anti-TNF-α therapy with ERT provided additional and unexpected benefits in the cartilage and bone of MPS animals, resulting in better clinical outcomes. Implementation of this therapy in MPS patients may be facilitated by the fact that several anti-TNF-α drugs are available for clinical use in other inflammatory conditions (e.g., Remicade®, etc). However, chronic use of these therapies in MPS patients also may have deleterious effects, and carefully controlled clinical trials will be necessary to determine the safety and efficacy of this combined treatment protocol. A second important finding is that ERT alone reduces TNF-α related inflammation, providing additional evidence that GAG storage in the MPS diseases is directly activating this pathway. Indeed, the general anti-inflammatory effect of ERT likely results in positive, secondary benefits to organs that the enzyme cannot reach. Lastly, the data reported here further validates the fact that TNF-α, RANKL and other inflammatory markers can be used as biomarkers to monitor the effects of therapies in the MPS diseases. Currently, the only biomarker that is widely used in these disorders is GAG release in the urine, and these simple serum assays may have considerable, additive benefits.

Example 10

Figures 7A, 7B, 7C, 7D, 7E, 7F:
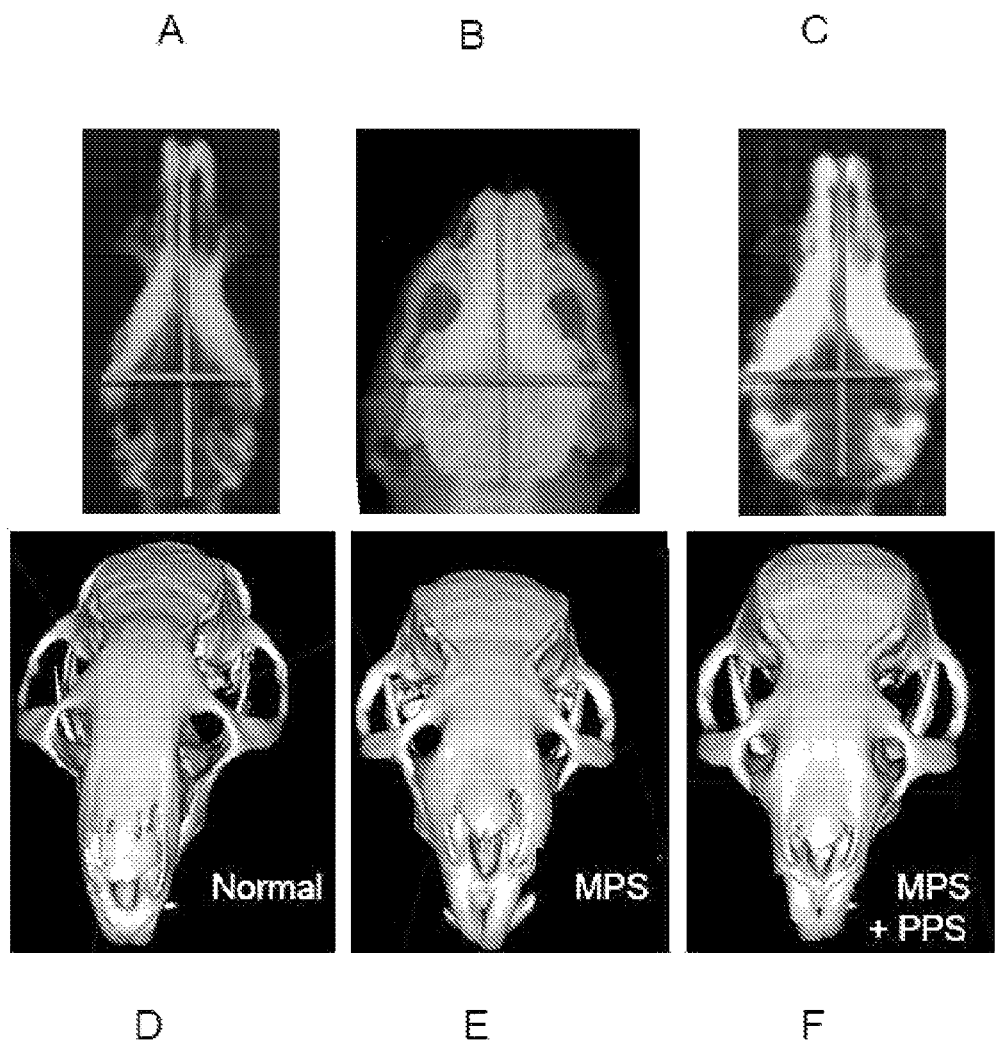
FIGS. 7A-7F show skull radiographs (FIGS. 7A, 7B, 7C) and microCT images (FIGS. 7D, 7E, 7F) of normal rats (FIGS. 7A, 7D), MPS VI rats with PPS treatment (FIGS. 7C, 7F), and MPS VI rats without PPS treatment (FIGS. 7B, 7E). MPS VI rats were maintained on normal watering or with water containing 25 mg/day PPS (n=6/group). Animals were 6 months of age when treatment was begun, and treatment was carried out for 3 months. The top images show radiographs (FIGS. 7A, 7B, 7C), and the bottom images microCT images (FIGS. 7D, 7E, 7F). Longer snouts and thinner skulls were found in the MPS VI rats treated with PPS compared to untreated MPS VI. The lines in the radiographs are for reference. The quantitative data shown in FIGS. 6A-6D on skull length and width were measured from these radiographs.

Preliminary Studies on the Effects of Anti-TNF-α Therapy on Enzyme Replacement Therapy in Pentosan Polysulfate In order to develop "proof-of-principle" data, six MPS VI rats at 6 months of age were treated with PPS for 3 months. 6-month-old MPS VI rats have established bone, cartilage, and inflammatory disease, and the specific goal in this initial study was therefore to evaluate whether PPS could either slow or reverse any of the clinical or pathological findings in MPS animals with advanced disease. As can be seen in FIGS. 6A-6D, the facial appearance of the treated 9-month-old MPS VI animals was markedly different from untreated MPS VI control animals. As illustrated by FIGS. 7A-7F skull radiographs and microCT images were taken of normal rats (FIGS. 7A, 7D), MPS VI rats with PPS treatment (FIGS. 7C, 7F), and MPS VI rats without PPS treatment (FIGS. 7B, 7E). The skulls of the treated animals (FIGS. 7C, 7F) were longer, the eyes, which are normally bulging in MPS VI due the abnormal optical orbits, were recessed like normal, and there were markedly fewer ocular porphyrin secretions. The images shown are representative of the general observations on these animals. Skull radiographs confirmed these observations, and revealed significantly longer skulls and snouts in the treatment group (i.e., those treated with PPS), despite the advanced age at which treatment was initiated (FIGS. 7A-7F).

Figures 8A, 8B, 8C, 8D, 8E, 8F:
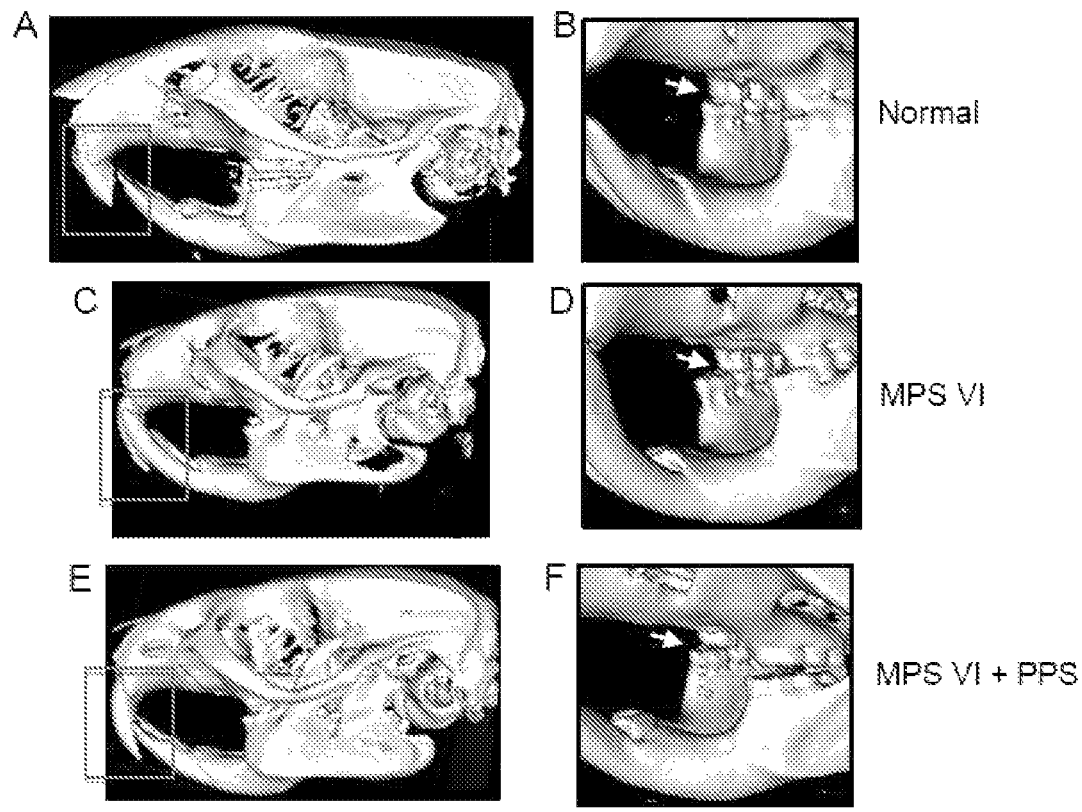
FIGS. 8A-8F show microCT images of normal rats (FIGS. 8A, 8B) MPS VI rats with PPS treatment (FIGS. 8E, 8F) and without PPS treatment (FIGS. 8C, 8D) showing dentition changes. MPS VI rats were maintained on normal watering or with water containing 25 mg/day PPS (n=6/group). Animals were 6 months of age when treatment was begun, and treatment was carried out for 3 months. Untreated MPS VI rats have overgrown incisors (box) that leads to abnormal alignment of the teeth compared to normal rats. The mandible and misalignment were corrected by PPS treatment.

MicroCT images further supported these observations, as shown in FIGS. 8A-8F. MPS VI rats with PPS treatment (FIGS. 8E, 8F) and without PPS treatment (FIGS. 8C, 8D) showed dentition changes. MPS VI rats without PPS treatment (FIGS. 8C, 8D) as compared to MPS VI rats with PPS treatment (FIGS. 8E, 8F) displayed overgrown incisors (box) that leads to abnormal alignment of the teeth compared to normal rats (FIGS. 8A-8F). MicroCT images of normal rats are shown in FIGS. 8A, 8B. Untreated MPS VI rats have overgrown incisors (box) (FIGS. 8C, 8D) that leads to abnormal alignment of the teeth compared to normal rats. The mandible and misalignment were corrected by PPS treatment (FIGS. 8E, 8F).

Figure 9:
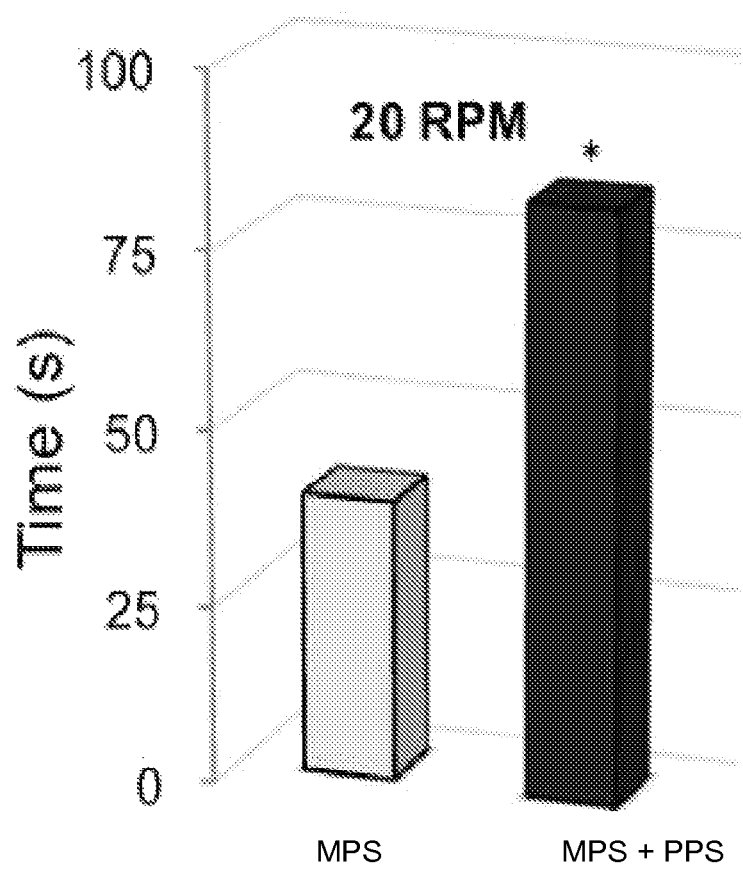
FIG. 9 depicts rotarod analysis of MPS VI rats with and without PPS. Six-month-old MPS VI rats were maintained with or without PPS for 3 months (n=6/group), and prior to sacrifice were analyzed using an accelerating rotarod apparatus. Gray=MPS VI rats on normal water; Blue=MPS VI rats receiving PPS. Note that the treated MPS VI rats could remain on the rotating rod more than twice as long as untreated rats. *=p<0.02.
Figures 10A, 10B:
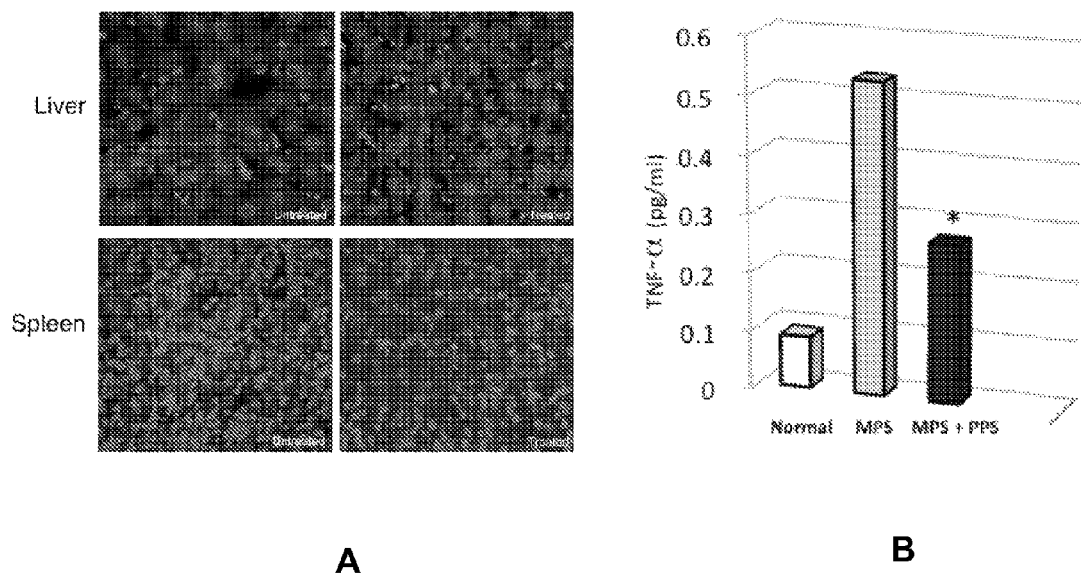
FIGS. 10A-10B illustrate immunohistochemical analysis of PPS treated and untreated rats.
Figures 11A, 11B, 11C:
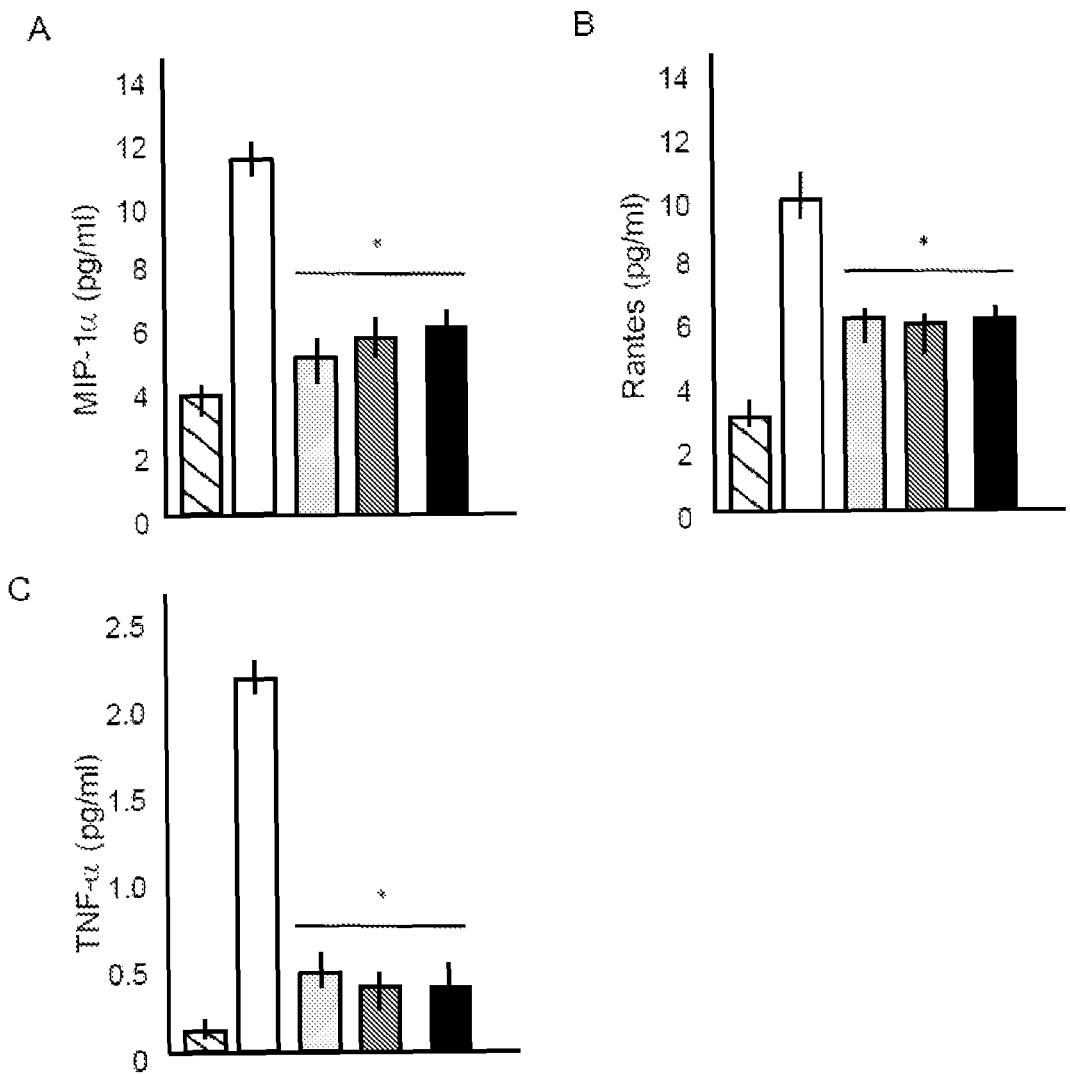
FIGS. 11A-11C show serum inflammatory markers in treated and untreated MPS VI rats. Three groups of MPS VI rats were treated with PPS beginning at six months (light gray), one month (dark gray) or prenatally (black). All animals were sacrificed at 9 months of age. The duration of treatment was therefore 3 months, 8 months or 9.75 months, respectively. The serum levels of several inflammatory markers were measured by ELISA assays, and compared to normal (hatched) or untreated MPS VI animals (white). N=6/group. Serum levels of inflammatory marker MIP-1α is shown in FIG. 11A, while levels of marker Rantes is shown in FIG. 11B and levels of TNF-α are shown in FIG. 11C. All treatment groups had significantly (<0.001) lower levels of these inflammatory markers compared to untreated MPS VI rats.

Immediately prior to sacrifice, the animals also were studied using an accelerating rotarod apparatus. As can be seen in FIG. 9, the MPS VI rats that were treated with PPS for 3 months remained on the rotarod significantly longer than the untreated control animals. It was hypothesized that this reflects either increased joint mobility and/or reduced inflammation and pain in the treatment group. In addition, immunohistochemical analysis showed that TNF-levels were reduced in the liver and spleen, and the levels of this cytokine were similarly reduced in the blood (FIGS. 10A-10B). ELISA assays showed that serum inflammatory markers in treated MPS VI rats were significantly lower than those inflammatory marker levels in untreated MPS VI rats (FIGS. 11A-11C). Serum levels of inflammatory marker MIP-1α is shown in FIG. 11A, while levels of marker Rantes is show in FIG. 11B and levels of TNF-α are shown in FIG. 11C.

Figures 12A, 12B, 12C:
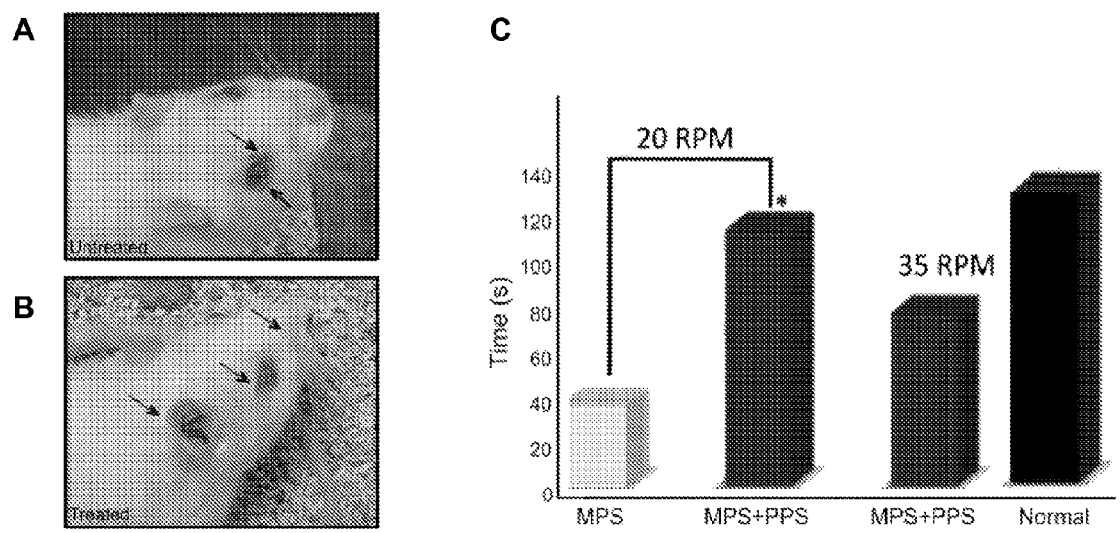
FIGS. 12A-12C show results of treatment of MPS VI rats at one month of age.
Figure 13:
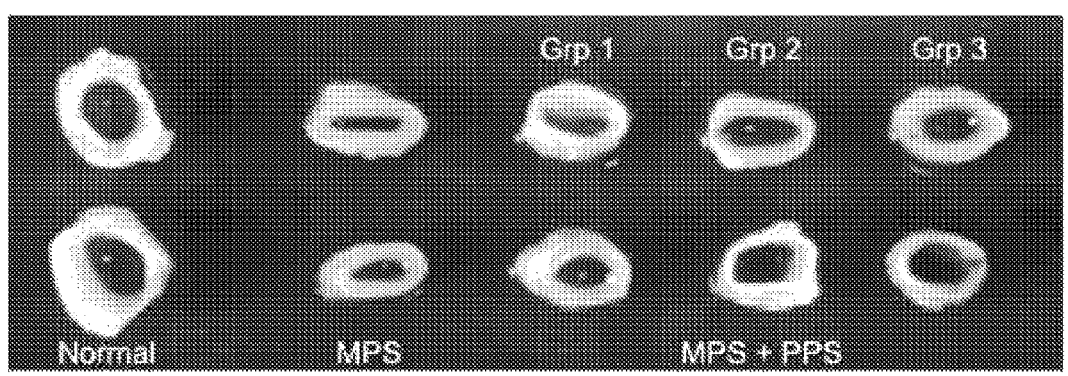
FIG. 13 illustrates tracheas of MPS VI rats treated with PPS. Groups 1, 2 and 3 animals were treated with PPS beginning at 6 months, 1 month, and prenatally. They were sacrificed at 9 months and the tracheas were isolated. The images show that untreated MPS VI rats have collapsed tracheas compared to normal, and that this was improved in all of the PPS treatment groups.

PPS treatment in MPS VI rats at 1 month of age was also initiated, and similar to what was observed with the older animals there was a significant effect on facial appearance, skull length, eye and nasal secretions, and motility as assessed by rotarod performance (FIGS. 12A-12C). Tracheas of MPS VI rats that were not treated with PPS showed collapsed tracheas as compared to normal tracheas, while this was improved in all of the PPS treatment groups (FIG. 13).

Figures 14A, 14B, 14C:
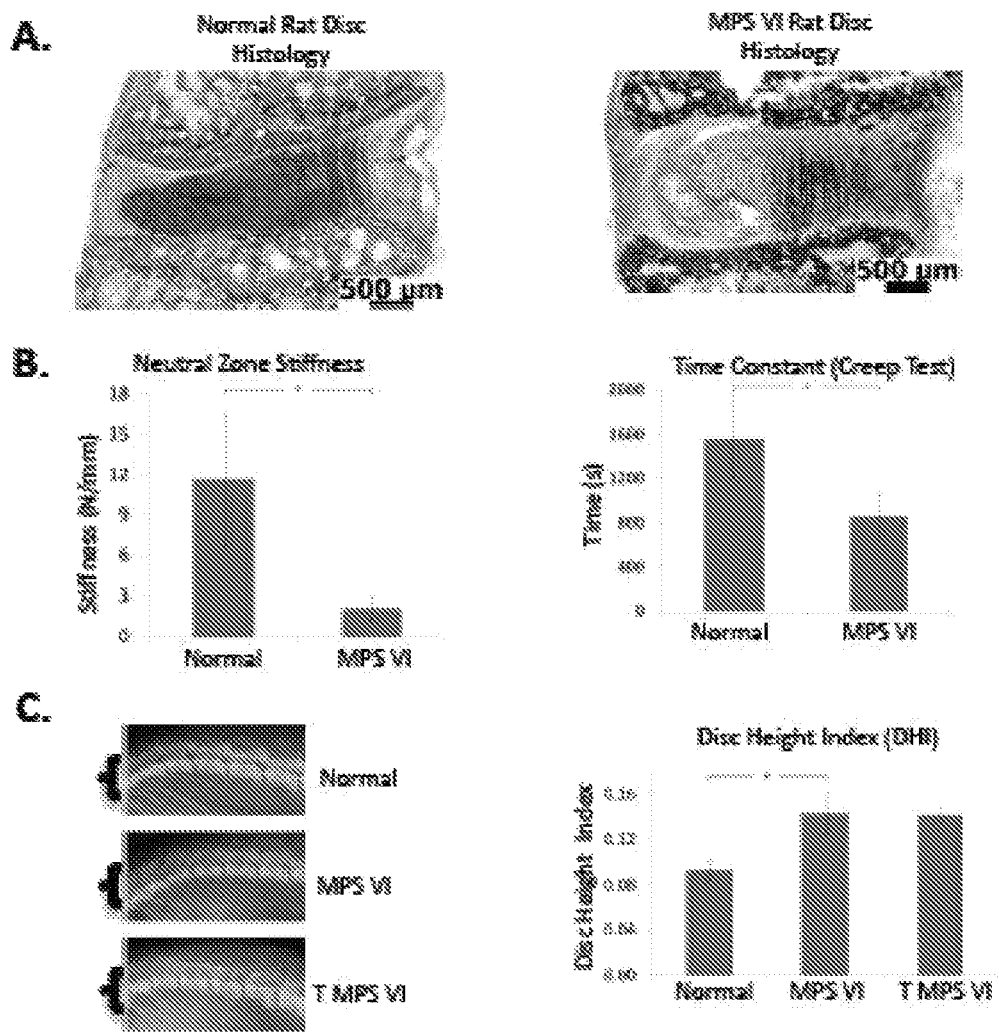
FIGS. 14A-14C show an assessment of spine disease in the treated (6 month old) and untreated MPS VI rats.
Figure 15:
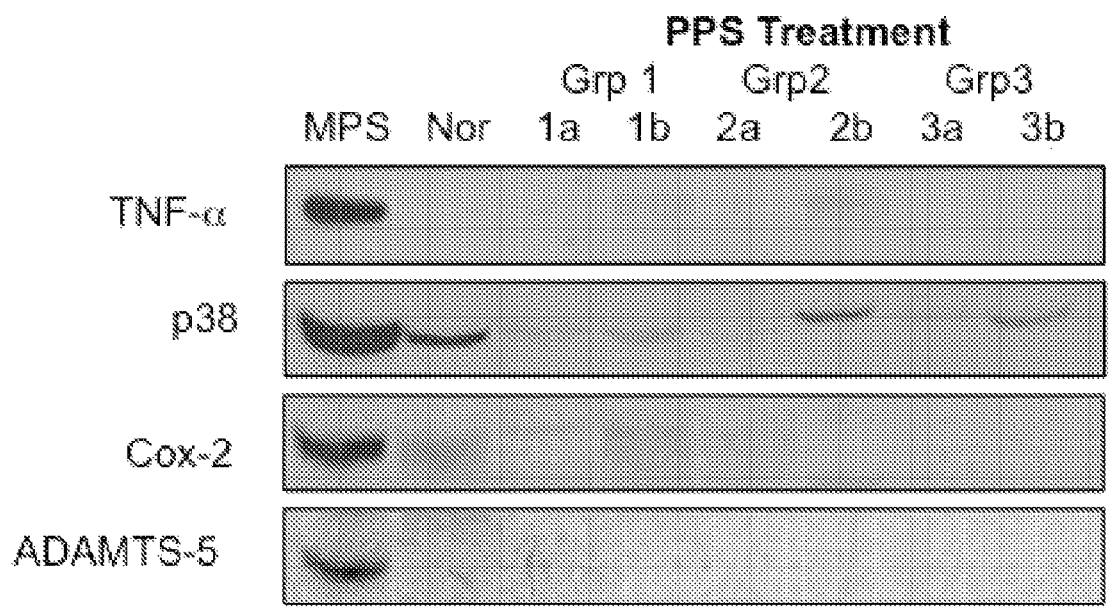
FIG. 15 shows an analysis of articular chondrocytes in PPS treated MPS VI rats. Groups 1, 2 and 3 animals were treated with PPS beginning at 6 months, 1 month and prenatally. They were sacrificed at 9 months and articular chondrocytes were isolated and grown for 3 weeks. They were then analyzed by western blotting. Note that the inflammatory markers, TNF-α, p38 and Cox-2 were elevated in MPS VI rat chondrocytes compared to normal, and that these levels were reduced to normal in the treated MPS VI rats. ADAMTS-5 is a proteeoglycan-degrading aggrecanase that also is elevated in untreated MPS VI rat chondrocytes, and was reduced in the MPS VI treatment groups.
Figure 16:
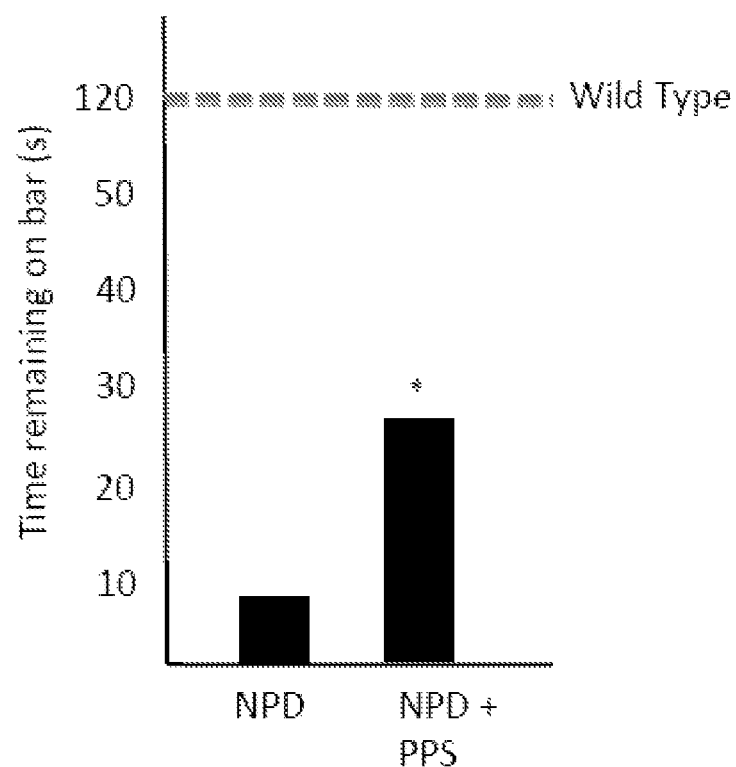
FIG. 16 shows a rotarod analysis of Niemann-Pick disease mice treated with PPS. One-month-old Niemann-Pick disease mice (acid sphingomyelinase knock-out) were treated with PPS for three months beginning at one month of age (25 mg/kg/day). They were then analyzed using an accelerating rotarod apparatus set to 20 RPM. The NPD mice treated with PPS performed significantly better (p<0.01) than those without treatment. Both groups remained significantly below wild-type.

Lastly, spine disease in the treated (6 month old) and untreated MPS VI rats was assessed. These studies have documented several important and clinically relevant endpoints that can be followed during PPS treatment. Histologically, MPS VI discs had abundant, enlarged vacuolated nuclear and annular cells as well as thickened annulus layers, focal defects in the nucleus pulposus, and increased disc height as compared to control discs (FIG. 14A). Biomechanically, compared to normal spinal segment, the cyclic tension-compression (Creep) test showed that the MPS VI motion segment had significantly decreased neutral zone (447.9%; FIG. 14B) and tensile stiffness (110.0%). The Creep test also showed a significantly smaller time constant in MPS VI samples (82.8%; FIG. 14B). Articular chondrocytes in MPS VI rats that were not treated with PPS show elevated TNF-α, p38 and Cox-2 compared to normal, but those levels were reduced to normal in the treated MPS VI rats (FIG. 15). ADAMTS-5 is a proteoglycan-degrading aggrecanase that also is elevated in untreated MPS VI rat chondrocytes, but was reduced in the MPS VI treatment groups (FIG. 15). A rotarod analysis illustrated that one-month-old Niemann-Pick disease mice (acid sphingomyelinase knock-out) that were treated with PPS for three months performed significantly better than those Niemann-Pick disease mice without treatment (FIG. 16).

Overall, the MPS VI animals demonstrated substantial changes in spinal motion segment biomechanics and disc structure which may be associated with the development and progression of the spinal pathology observed in the MPS population. The integrity of the nucleus pulposus and annulus fibrosus are important to sustain the normal biomechanical function of the vertebral segment. The sizable defects in these structures in the MPS VI rats may be associated with decreased biomechanical function, as represented by reduced neutral zone stiffness. The decrease in time constant (creep time) also revealed there was an alteration of intervertebral water transport and retention capacity, which might likely to be related to dysfunctional GAGs, but could also be partly associated with alterations in endplate permeability and collagen function, as reported for the MPS VII canine model.

Of note, PPS did not restore the increased disc height index (DHI) in the treated MPS VI animals with advanced disease (FIG. 14C), despite its positive effects on skull and snout lengths, rotarod performance and inflammation (FIGS. 6A-6D, 9, 10A-10B, 12A-12C). This finding reveals the importance of early screening and intervention for the treatment of this (and perhaps other) parameters in MPS, and the need to carefully evaluate the effects of drug treatment as a function of age and disease progression.

Since PPS is a GAG-like polysaccharide, it would not have been expected to be therapeutically useful in the MPS GAG storage disorders. The positive results in the MPS VI animals were, therefore, surprisingly unexpected. In addition, since PPS is not known to cross the blood brain barrier, it would not have been expected to have positive neurological effects (like those exhibited in FIG. 16) in the Niemann-Pick disease mouse model.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of treating a subject with a lysosomal storage disorder, said method comprising:
    selecting a subject with a lysosomal storage disorder and administering to the selected subject an agent for an enzyme replacement therapy, and an agent for an anti-TNF-α treatment under conditions effective to treat the lysosomal storage disorder in the selected subject.

2. The method of claim 1, wherein the agent for anti-TNF-α therapy is pentosan polysulfate (PPS).

3. The method of claim 1 further comprising:
    administering an additional therapy.

4. A method of reducing inflammatory cytokines in a subject with a lysosomal storage disorder that is being treated by an enzyme replacement therapy, said method comprising:
    administering to the subject an agent for an anti-TNF-α treatment under conditions effective to reduce the inflammatory cytokines in the subject.

5. The method of claim 4 further comprising:
    selecting a subject with a skeletal pathology associated with a lysosomal storage disorder to be subjected to said administering.

6. The method of claim 4, wherein the agent for anti-TNF-α therapy is pentosan polysulfate (PPS).

7. A method of treating a subject with a lysosomal storage disorder, said method comprising:
    selecting a subject with a lysosomal storage disorder and administering pentosan polysulfate (PPS) to the selected subject under conditions effective to treat the lysosomal storage disorder in the selected subject.

8. The method of claim 7 further comprising:
administering an additional therapy.

9. The method of claim 8, wherein the additional therapy is selected from the group consisting of bone marrow transplant, chaperone therapy, and gene therapy.

10. The method of claim 7, wherein the lysosomal storage disorder is selected from the group consisting of sphingolipidoses, mucopolysaccharide storage disease (mucopolysaccharidoses), glycoproteinoses, mucolipidoses, glycogenosis type II, ceroid lipofuscinoses, and other abnormalities of lysosomal protein function.

11. The method of claim 7, wherein the lysosomal storage disorder is a sphingolipidosis, said sphingolipidosis being Niemann-Pick disease.

12. The method of claim 7, wherein the lysosomal storage disorder is a mucopolysaccharidosis, said mucopolysaccharidosis being MPS I (Hurler/Schie Syndrome), MPS II (Hunter Syndrome), MPS VI (Maroteaux-Lamy Syndrome), MPS III (Sanfilippo Syndrome), MPS IV (Morquio Syndrome), or MPS VII (Sly Disease).

13. The method of claim 7, wherein said administering is carried out orally, by inhalation, by intranasal instillation, topically, transdermally, parenterally, subcutaneously, by intravenous injection, by intra-arterial injection, by intramuscular injection, intraplurally, intraperitoneally, or by application to mucous membrane.

14. The method of claim 7 further comprising:
repeating said administering.

15. The method of claim 7, wherein the subject is an infant or juvenile.

16. The method of claim 7, wherein the subject is an adult.

17. The method of claim 7, wherein the subject has a skeletal pathology associated with a lysosomal storage disorder.

18. A method of treating a subject with a skeletal pathology associated with a lysosomal storage disorder, said method comprising:
selecting a subject with a skeletal pathology associated with a lysosomal storage disorder and
administering to the selected subject an agent for substrate reduction therapy and an agent for an anti-TNF-α treatment under conditions effective to treat the skeletal pathology associated with lysosomal storage disorder in the subject.

19. The method of claim 18, wherein the agent anti-TNF-α therapy is pentosan polysulfate (PPS).

20. The method of claim 18 further comprising:
administering an additional therapy.

* * * * *